US010675027B2

(12) United States Patent
Aldridge et al.

(10) Patent No.: US 10,675,027 B2
(45) Date of Patent: Jun. 9, 2020

(54) SURGICAL INSTRUMENT WITH SELECTABLE INTEGRAL OR EXTERNAL POWER SOURCE

(71) Applicant: ETHICON LLC, Guaynabo, PR (US)

(72) Inventors: Jeffrey L. Aldridge, Lebanon, OH (US); Eitan T. Wiener, Cincinnati, OH (US); Robert A. Kemerling, Mason, OH (US); James R. Giordano, Milford, OH (US); Vincent P. Battaglia, Jr., Lebanon, OH (US); Daniel W. Price, Loveland, OH (US); Sean P. Conlon, Loveland, OH (US); Gregory W. Johnson, Milford, OH (US); Jeffrey D. Messerly, Cincinnati, OH (US); Shan Wan, Mason, OH (US); Kevin L. Houser, Springboro, OH (US); Foster B. Stulen, Mason, OH (US); Jacob S. Gee, Cincinnati, OH (US); Jeffrey A. Bullock, Cincinnati, OH (US); John A. Hibner, Mason, OH (US); William B. Weisenburgh, II, Maineville, OH (US)

(73) Assignee: Ethicon LLC, Guaynabo, PR (US)

( * ) Notice: Subject to any disclaimer, the term of this patent is extended or adjusted under 35 U.S.C. 154(b) by 0 days.

(21) Appl. No.: 15/680,484

(22) Filed: Aug. 18, 2017

(65) Prior Publication Data

US 2018/0028182 A1 Feb. 1, 2018

Related U.S. Application Data

(62) Division of application No. 13/804,417, filed on Mar. 14, 2013, now abandoned.

(Continued)

(51) Int. Cl.
*A61B 17/072* (2006.01)
*A61B 18/14* (2006.01)
(Continued)

(52) U.S. Cl.
CPC .. *A61B 17/07207* (2013.01); *A61B 17/00234* (2013.01); *A61B 18/1445* (2013.01);
(Continued)

(58) Field of Classification Search
None
See application file for complete search history.

(56) References Cited

U.S. PATENT DOCUMENTS 3,079,510 A 2/1963 Hartwig
4,091,880 A 5/1978 Troutner et al.
(Continued)

FOREIGN PATENT DOCUMENTS

CN 1578055 2/2005
DE 102005015654 10/2006
(Continued)

OTHER PUBLICATIONS

Chinese Office Action, Notification of the First Office Action, and Search Report dated Feb. 24, 2017 for Application No. CN 201480005656.0, 10 pgs.
(Continued)

*Primary Examiner* — Carl H Layno
*Assistant Examiner* — Manolis Pahakis
(74) *Attorney, Agent, or Firm* — Frost Brown Todd LLC

(57) ABSTRACT

A surgical instrument includes a body, a shaft, and an end effector. The shaft extends distally from the body. The end effector is located at a distal end of the shaft. The end effector includes an active feature configured to operate on tissue. The body includes a drive feature operable to drive the active feature of the end effector. The body is operable
(Continued)

to selectively couple with a variety of power sources such that the drive feature may receive electrical power form a battery or from a corded power source, based on a user's preference. The body may include a handpiece that has a socket configured to receive a battery or cable adapter. The body may removably receive various kinds of shaft assemblies to provide various operating modalities. The shaft assemblies may include user interface features.

20 Claims, 18 Drawing Sheets

Related U.S. Application Data

(60) Provisional application No. 61/755,607, filed on Jan. 23, 2013.

(51) Int. Cl.
| | | |
|---|---|---|
| *A61B 17/00* | (2006.01) | |
| *A61B 17/32* | (2006.01) | |
| *A61B 18/00* | (2006.01) | |
| *A61B 18/12* | (2006.01) | |
| *A61B 17/29* | (2006.01) | |
| *H01M 2/10* | (2006.01) | |
| *H01R 13/66* | (2006.01) | |

(52) U.S. Cl.
CPC ...... *H01M 2/1066* (2013.01); *H01R 13/6675* (2013.01); *A61B 2017/00017* (2013.01); *A61B 2017/00026* (2013.01); *A61B 2017/0046* (2013.01); *A61B 2017/00115* (2013.01); *A61B 2017/00119* (2013.01); *A61B 2017/00221* (2013.01); *A61B 2017/00225* (2013.01); *A61B 2017/00398* (2013.01); *A61B 2017/00411* (2013.01); *A61B 2017/00464* (2013.01); *A61B 2017/00734* (2013.01); *A61B 2017/2927* (2013.01); *A61B 2017/320093* (2017.08); *A61B 2017/320094* (2017.08); *A61B 2017/320095* (2017.08); *A61B 2017/320097* (2017.08); *A61B 2018/00791* (2013.01); *A61B 2018/1226* (2013.01); *A61B 2560/0443* (2013.01); *H01M 2220/30* (2013.01); *H01R 2201/12* (2013.01)

(56) References Cited

U.S. PATENT DOCUMENTS

| | | | |
|---|---|---|---|
| 4,570,832 A | | 2/1986 | Kroger |
| 4,598,709 A | | 7/1986 | Smith et al. |
| 4,793,345 A | | 12/1988 | Lehmer |
| 4,835,410 A | | 5/1989 | Bhagwat et al. |
| 4,878,493 A | | 11/1989 | Pasternak et al. |
| 5,322,055 A | | 6/1994 | Davison et al. |
| 5,474,451 A | | 12/1995 | Dalrymple et al. |
| 5,779,702 A | | 7/1998 | Fard |
| 5,796,188 A | * | 8/1998 | Bays .............. A61B 17/1628 310/40 MM |
| 5,873,873 A | | 2/1999 | Smith et al. |
| 5,980,510 A | | 11/1999 | Tsonton et al. |
| 6,007,373 A | | 12/1999 | Chew |
| 6,056,735 A | | 5/2000 | Okada et al. |
| 6,104,162 A | | 8/2000 | Sainsbury et al. |
| 6,172,860 B1 | | 1/2001 | Yoshimizu et al. |
| 6,237,698 B1 | | 5/2001 | Carrier et al. |
| 6,251,110 B1 | | 6/2001 | Wampler |
| 6,325,811 B1 | | 12/2001 | Messerly |
| 6,500,176 B1 | | 12/2002 | Truckai et al. |
| 6,783,524 B2 | | 8/2004 | Anderson et al. |
| 6,883,621 B1 | | 4/2005 | Lin |
| 7,112,201 B2 | | 9/2006 | Truckai et al. |
| 7,125,409 B2 | | 10/2006 | Truckai et al. |
| 7,169,146 B2 | | 1/2007 | Truckai et al. |
| 7,186,253 B2 | | 3/2007 | Truckai et al. |
| 7,189,233 B2 | | 3/2007 | Truckai et al. |
| 7,196,911 B2 | | 3/2007 | Takano et al. |
| 7,220,951 B2 | | 5/2007 | Truckai et al. |
| 7,309,849 B2 | | 12/2007 | Truckai et al. |
| 7,311,709 B2 | | 12/2007 | Truckai et al. |
| 7,354,440 B2 | | 4/2008 | Truckai et al. |
| 7,381,209 B2 | | 6/2008 | Truckai et al. |
| 7,416,101 B2 | | 8/2008 | Shelton, IV et al. |
| 8,029,510 B2 | | 10/2011 | Hoegerle |
| 8,246,608 B2 | | 8/2012 | Omori et al. |
| 8,403,950 B2 | | 3/2013 | Palmer et al. |
| 8,453,914 B2 | | 6/2013 | Laurent et al. |
| 8,461,744 B2 | | 6/2013 | Wiener et al. |
| 9,050,083 B2 | | 6/2015 | Yates et al. |
| 9,414,849 B2 | | 8/2016 | Nagashimada |
| 9,439,649 B2 | | 9/2016 | Shelton, IV et al. |
| 2002/0128644 A1 | * | 9/2002 | Hata .............. A61B 18/14 606/34 |
| 2003/0032950 A1 | | 2/2003 | Altshuler et al. |
| 2004/0081939 A1 | | 4/2004 | Rosenstatter |
| 2004/0199155 A1 | | 10/2004 | Mollenauer |
| 2005/0165458 A1 | | 7/2005 | Boveja et al. |
| 2006/0079874 A1 | | 4/2006 | Faller et al. |
| 2007/0191713 A1 | | 8/2007 | Eichmann et al. |
| 2007/0282333 A1 | | 12/2007 | Fortson et al. |
| 2008/0103491 A1 | | 5/2008 | Omori et al. |
| 2008/0147058 A1 | | 6/2008 | Horrell et al. |
| 2008/0200940 A1 | | 8/2008 | Eichmann et al. |
| 2008/0262654 A1 | | 10/2008 | Omori et al. |
| 2009/0030428 A1 | | 1/2009 | Omori et al. |
| 2009/0108048 A1 | | 4/2009 | Zemlok et al. |
| 2009/0143803 A1 | | 6/2009 | Palmer et al. |
| 2009/0209990 A1 | | 8/2009 | Yates et al. |
| 2009/0264887 A1 | | 10/2009 | Beale et al. |
| 2009/0292305 A1 | | 11/2009 | Kahler et al. |
| 2010/0069940 A1 | | 3/2010 | Miller et al. |
| 2010/0230465 A1 | | 9/2010 | Smith et al. |
| 2011/0009699 A1 | | 1/2011 | Slenker et al. |
| 2011/0015627 A1 | | 1/2011 | DiNardo et al. |
| 2011/0015631 A1 | | 1/2011 | Wiener et al. |
| 2011/0022032 A1 | | 1/2011 | Zemlok et al. |
| 2011/0064978 A1 | | 3/2011 | McGahan et al. |
| 2011/0087212 A1 | | 4/2011 | Aldridge et al. |
| 2011/0087218 A1 | | 4/2011 | Boudreaux et al. |
| 2011/0087256 A1 | | 4/2011 | Wiener et al. |
| 2011/0245833 A1 | | 10/2011 | Anderson |
| 2012/0078243 A1 | | 3/2012 | Worrell et al. |
| 2012/0078247 A1 | | 3/2012 | Worrell et al. |
| 2012/0110810 A1 | | 5/2012 | Houser et al. |
| 2012/0112687 A1 | | 5/2012 | Houser et al. |
| 2012/0115005 A1 | | 5/2012 | Stulen et al. |
| 2012/0116260 A1 | | 5/2012 | Johnson et al. |
| 2012/0116265 A1 | | 5/2012 | Houser et al. |
| 2012/0116266 A1 | | 5/2012 | Houser et al. |
| 2012/0116267 A1 | | 5/2012 | Kimball et al. |
| 2012/0116363 A1 | | 5/2012 | Houser et al. |
| 2012/0116364 A1 | | 5/2012 | Houser et al. |
| 2012/0116365 A1 | | 5/2012 | Price et al. |
| 2012/0116367 A1 | | 5/2012 | Houser et al. |
| 2012/0116379 A1 | | 5/2012 | Yates et al. |
| 2012/0116380 A1 | | 5/2012 | Madan et al. |
| 2012/0116381 A1 | | 5/2012 | Houser et al. |
| 2012/0116388 A1 | | 5/2012 | Houser et al. |
| 2012/0116389 A1 | | 5/2012 | Houser et al. |
| 2012/0116394 A1 | | 5/2012 | Timm et al. |
| 2012/0116395 A1 | | 5/2012 | Madan et al. |
| 2012/0116396 A1 | | 5/2012 | Price et al. |
| 2012/0310229 A1 | | 12/2012 | Gregg |
| 2013/0023868 A1 | | 1/2013 | Worrell et al. |
| 2013/0030428 A1 | | 1/2013 | Worrell et al. |
| 2013/0090577 A1 | | 4/2013 | Boudreaux et al. |
| 2013/0103023 A1 | | 4/2013 | Monson et al. |
| 2013/0184730 A1 | | 7/2013 | Beardsley et al. |
| 2013/0253499 A1 | | 9/2013 | Kimball et al. |
| 2013/0324998 A1 | | 12/2013 | Kimball et al. |

(56) References Cited

U.S. PATENT DOCUMENTS

| | | |
|---|---|---|
| 2014/0012263 A1 | 1/2014 | Marzella |
| 2014/0207124 A1 | 7/2014 | Aldridge et al. |
| 2014/0309666 A1 | 10/2014 | Shelton, IV et al. |

FOREIGN PATENT DOCUMENTS

| | | |
|---|---|---|
| JP | H11-299801 A | 11/1999 |
| JP | 2000-262533 A | 9/2000 |
| JP | 2010-088876 A | 4/2010 |
| WO | WO 98/006144 A1 | 2/1998 |
| WO | WO 2012/037096 A2 | 3/2012 |
| WO | WO 2012/166717 | 12/2012 |

OTHER PUBLICATIONS

Micro Digital, Full Wave Bridge Rectifier Supply, Dec. 3, 2012, obtained from the Wayback Machine using link: http://www.micro-digital.net/full-wave-bridge-rectifier-supply.

International Search Report and Written Opinion for PCT Application No. PCT/US2014/011638 dated Apr. 11, 2014.

International Preliminary Report on Patentability for PCT Application No. PCT/US2014/011638 dated Jul. 28, 2015.

U.S. Appl. No. 13/426,760, filed Mar. 22, 2012.
U.S. Appl. No. 13/426,792, filed Mar. 22, 2012.
U.S. Appl. No. 13/484,547, filed May 31, 2012.
U.S. Appl. No. 13/716,308, filed Dec. 17, 2012.
U.S. Appl. No. 13/804,417, filed Mar. 14, 2013.
U.S. Appl. No. 61/410,603, filed Nov. 5, 2010.
U.S. Appl. No. 61/755,607, filed Jan. 23, 2013.

Australian Office Action, Examination Report No. 1 for standard parent application, dated Jul. 17, 2017 for Application No. AU 2014209739, 3 pgs.

Brazilian Office Action dated Jan. 6, 2020 for a No. BR112015017542-2, 4 pgs.

Canadian Office Action dated Nov. 28, 2019 for Application No. CA 2,899,161, 3 pgs.

Chinese Office Action, the Second Office Action, dated Nov. 1, 2018 for Application No. CN 201480005656.0, 4 pgs.

European Examination Report dated Oct. 20, 2016 for Application No. EP 14703669.3, 4 pgs.

Japanese Office Action, Decision to Grant a Patent, dated May 15, 2018 for Application No. 1 JP 2015-555186, 2 pgs.

Japanese Office Action, Notice of Reasons for Refusal, and Search Report by registered Search Organization dated Oct. 24, 2017 for Application No. JP 2015-555186, 25 pgs.

\* cited by examiner

SURGICAL INSTRUMENT WITH SELECTABLE INTEGRAL OR EXTERNAL POWER SOURCE

PRIORITY

This application is a divisional application of U.S. Nonprovisional patent application Ser. No. 13/804,417, filed Mar. 14, 2013, now abandoned, which claims priority to U.S. Provisional Pat. App. No. 61/755,607, entitled "Surgical Instrument with Selectable Integral or External Power Source," filed Jan. 23, 2013, the disclosure of which is incorporated by reference herein.

BACKGROUND

A variety of surgical instruments rely at least in part on electrical power to operate. Examples of such instruments include some versions of surgical stapling and cutting instruments, ultrasonic surgical instruments, and electrosurgical instruments. An example of an electrically powered surgical stapling and cutting instrument is the ECHELON FLEX™ Powered ENDOPATH® Stapler by Ethicon Endo-Surgery, Inc. of Cincinnati, Ohio. Further examples of such devices and related concepts are disclosed in U.S. Pat. No. 7,416,101 entitled "Motor-Driven Surgical Cutting and Fastening Instrument with Loading Force Feedback," issued Aug. 26, 2008, the disclosure of which is incorporated by reference herein; U.S. Pub. No. 2009/0209990 entitled "Motorized Surgical Cutting and Fastening Instrument Having Handle Based Power Source," published Aug. 20, 2009, issued as U.S. Pat. No. 8,657,174 on Feb. 25, 2014, the disclosure of which is incorporated by reference herein; U.S. Pub. No. 2012/0239012, entitled "Motor-Driven Surgical Cutting Instrument with Electric Actuator Directional Control Assembly," published Sep. 20, 2012, and issued as U.S. Pat. No. 8,453,914 on Jun. 4, 2013, the disclosure of which is incorporated by reference herein; and U.S. patent application Ser. No. 13/716,308, entitled "Circular Stapler with Selectable Motorized and Manual Control," filed Dec. 17, 2012, issued as U.S. Pat. No. 9,445,816 on Sep. 20, 2016, the disclosure of which is incorporated by reference herein.

Examples of ultrasonic surgical instruments include the HARMONIC ACE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055 entitled "Clamp Coagulator/Cutting System for Ultrasonic Surgical Instruments," issued Jun. 21, 1994, the disclosure of which is incorporated by reference herein; U.S. Pat. No. 5,873,873 entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811 entitled "Blades with Functional Balance Asymmetries for use with Ultrasonic Surgical Instruments," issued Dec. 4, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004; U.S. Pub. No. 2006/0079874 entitled "Tissue Pad for Use with an Ultrasonic Surgical Instrument," published Apr. 13, 2006, now abandoned, the disclosure of which is incorporated by reference herein; U.S. Pub. No. 2007/0191713 entitled "Ultrasonic Device for Cutting and Coagulating," published Aug. 16, 2007, now abandoned, the disclosure of which is incorporated by reference herein; U.S. Pub. No. 2007/0282333 entitled "Ultrasonic Waveguide and Blade," published Dec. 6, 2007, now abandoned, the disclosure of which is incorporated by reference herein; U.S. Pub. No. 2008/0200940 entitled "Ultrasonic Device for Cutting and Coagulating," published Aug. 21, 2008, now abandoned, the disclosure of which is incorporated by reference herein; U.S. Pub. No. 2010/0069940 entitled "Ultrasonic Device for Fingertip Control," published Mar. 18, 2010, issued as U.S. Pat. No. 9,023,071 on May 5, 2015, the disclosure of which is incorporated by reference herein; U.S. Pub. No. 2011/0015660, entitled "Rotating Transducer Mount for Ultrasonic Surgical Instruments," published Jan. 20, 2011, and issued as U.S. Pat. No. 8,461,744 on Jun. 11, 2013, the disclosure of which is incorporated by reference herein; and. Additionally, some of the foregoing surgical tools may include a cordless transducer such as that disclosed in U.S. Pub. No. 2012/0112687, entitled "Recharge System for Medical Devices," published May 10, 2012, issued as U.S. Pat. No. 9,381,058 on Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410, 603, filed Nov. 5, 2010, entitled "Energy-Based Surgical Instruments," the disclosure of which is incorporated by reference herein.

A variety of electrosurgical instruments include a tissue cutting element and one or more elements that transmit RF energy to tissue (e.g., to coagulate or seal the tissue). An example of such a device is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Additional examples of electrosurgical cutting instruments and related concepts are disclosed in U.S. Pub. No. 2011/0087218, entitled "Surgical Instrument Comprising First and Second Drive Systems Actuatable by a Common Trigger Mechanism," published Apr. 14, 2011, issued as U.S. Pat. No. 8,939,974 on Jan. 27, 2015, the disclosure of which is incorporated by reference herein; U.S. Pub. No. 2012/0116379, entitled "Motor Driven Electrosurgical Device with Mechanical and Electrical Feedback," published May 10, 2012, issued as U.S. Pat. No. 9,161,803 on Oct. 20, 2015, the disclosure of which is incorporated by reference herein; U.S. Pub. No. 2012/0078243, entitled "Control Features for Articulating Surgical Device," published Mar. 29, 2012, issued as U.S. Pat. No. 9,877,720 on Jan. 30, 2018, the disclosure of which is incorporated by reference herein; U.S. Pub. No. 2012/0078247, entitled "Articulation Joint Features for Articulating Surgical Device," published Mar. 29, 2012, issued as U.S. Pat. No. 9,402,682 on Aug. 2, 2016, the disclosure of which is incorporated by reference herein; U.S. patent application Ser. No. 13/622,729, entitled "Surgical Instrument with Multi-Phase Trigger Bias," filed Sep. 19, 2012, and published as U.S. Pub. No. 2013/0030428 on Jan. 31, 2013, issued as U.S. Pat. No. 9,089,327 on Jul. 28, 2015, the disclosure of which is incorporated by reference herein; U.S. patent application Ser. No. 13/622,735, entitled "Surgical Instrument with Contained Dual Helix Actuator Assembly," filed Sep. 19, 2012, and published as U.S. Pub. No. 2013/0023868 on Jan. 24, 2013, issued as U.S. Pat. No. 9,545,253 on Jan. 17, 2017, the disclosure of which is incorporated by reference herein; and U.S. patent application Ser. No. 13/658,784, entitled "Litz Wire Battery Powered Device," filed Oct. 23, 2012, and published as U.S. Pub. No. 2013/0103023 on Apr. 25, 2013, issued as U.S. Pat. No. 9,421,060 on Aug. 23, 2016, the disclosure of which is incorporated by reference herein.

While several electrically powered surgical instruments have been made and used, it is believed that no one prior to the inventor(s) has made or used the invention described herein and in any claims appended hereto.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
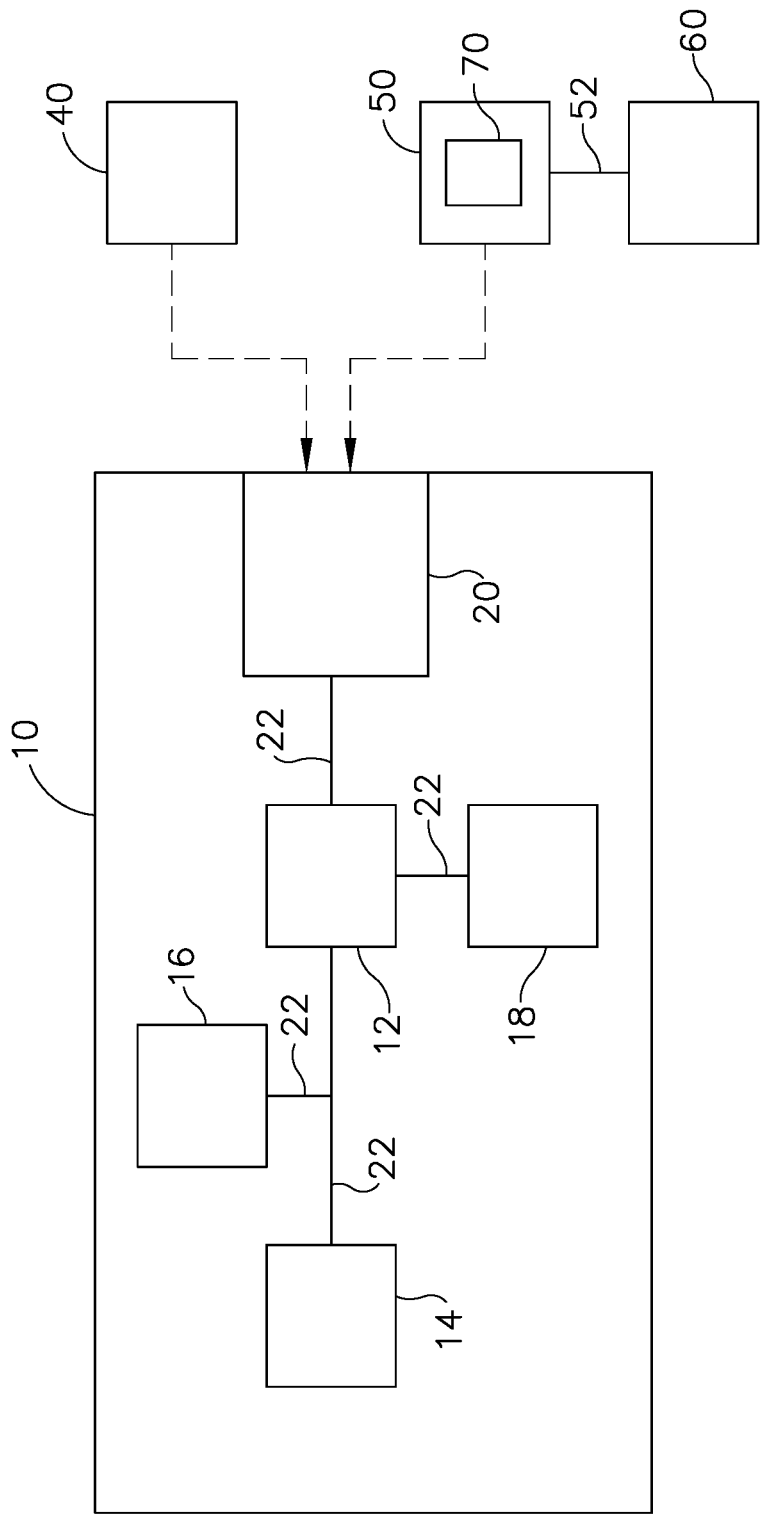
FIG. 1 depicts a block schematic view of an exemplary surgical instrument with interchangeable power source options.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Exemplary Surgical Instrument with Interchangeable Power Source Options

Those of ordinary skill in the art will recognize that battery powered devices may present their own advantages and disadvantages; while corded devices may present a different set of advantages and disadvantages. It may therefore be desirable in some instances to provide a device that is capable of providing the desired advantages of battery power or corded power, or perhaps avoiding disadvantages of battery power or corded power, based on the particular circumstances at hand. FIG. 1 illustrates an exemplary surgical instrument (10) that is capable of operating on battery power or corded power, as selected by the operator. Surgical instrument (10) of this example includes a control module (12), an end effector (14), a sensor (16), a user input (18), and a power socket (20). End effector (14), sensor (16), user input (18), and power socket (20) are all in communication with control module (12) via wires (22). Control module (12) is thus operable to receive inputs (e.g., power, data, etc.) from end effector (14), sensor (16), user input (18), and/or power socket (20); and to drive end effector (14) based on one or more control algorithms and based on input received from sensor (16) and/or user input (18). Control module (12) may comprise a microprocessor, an application specific integrated circuit (ASIC), memory, a printed circuit board (PCB), a storage device (such as a solid state drive or hard disk), firmware, software, and/or various other suitable components as will be apparent to those of ordinary skill in the art in view of the teachings herein. Wires (22) may comprise any suitable conventional wiring, traces in rigid circuit boards or flexible circuits, and/or any other suitable components that are operable to communicate electrical power and/or data/signals.

End effector (14) may include a variety of features that are operable to manipulate tissue. By way of example only, end effector (14) may include one or more movable jaws that are operable to grasp tissue, a tissue cutting feature (e.g., translating knife blade), a set of staples and staple drivers operable to sever tissue, an ultrasonic blade operable to denature proteins in tissue by applying ultrasonic energy to the tissue, one or more electrodes operable to provide RF energy (e.g., bipolar or monopolar) to tissue, and/or any other suitable features as will be apparent to those of ordinary skill in the art in view of the teachings herein. End effector (14) of this example comprises an active feature, such as an ultrasonic blade, a pair of clamping jaws, a sharp knife, a staple driving assembly, a monopolar RF electrode, a pair of bipolar RF electrodes, a thermal heating element, and/or various other components that may be driven by electrical power. In some instances, end effector (14) is removable from the rest of surgical instrument (10) for servicing, testing, replacement, or any other purpose as will be apparent to one of ordinary skill in the art in view of the teachings herein. It should also be understood that surgical instrument (10) may be configured to accept various kinds of end effectors (14) to perform different kinds of activities. For instance, surgical instrument (10) may accept a removable stapling end effector (14), which may be removed and replaced with an electrosurgical end effector (14), which may be removed and replaced with an ultrasonic end effector (14), and so on.

Sensor (16) of the present example is operable to provide a variety of information to control module (12) during a procedure. By way of example only, such configurations may include sensing a temperature at end effector (14) or determining the oscillation rate of end effector (14). Data from sensor (16) may be processed by control module (12) to effect the delivery of power to end effector (14) (e.g., in a feedback loop, etc.). Various other configurations of sensor (16) may be provided depending upon the purpose of surgical instrument (10) as will be apparent to those of ordinary skill in the art in view of the teachings herein. Various suitable uses for sensor (16) and various forms that sensor (16) may take will be apparent to those of ordinary skill in the art in view of the teachings herein. Of course, as with other components described herein, surgical instrument (10) may have more than one sensor (16); or sensor (16) may simply be omitted if desired.

Trigger (18) may be configured to selectively provide power from the selected power source (40, 60) to end effector (14) (and/or to some other component of surgical instrument (10)) to activate surgical instrument (10) when performing a procedure. By way of example only, trigger (18) may comprise one or more pushbuttons, one or more pivoting triggers, one or more sliders, one or more knobs, and/or variations and combinations thereof. Other suitable forms that trigger (18) may take will be apparent to those of ordinary skill in the art in view of the teachings herein.

Power socket (20) is operable to removably receive a power source (40, 50) and thereby power control module (12) and end effector (14). In particular, power socket (20) is operable to removably receive either a battery (40) or a plug (50). Power socket (20) may include electrical contacts, inductive coupling features, capacitive coupling features, and/or any other suitable type(s) of features that are operable to communicate power from power source (40, 50) to control module (12) when power source (40, 50) is fully coupled with power socket (20). Battery (40) may comprise a pack of one or more NiMH batteries, Li-ion batteries (e.g., prismatic cell type lithium ion batteries, etc.), Ni-Cad batteries, or any other type of portable power source as may be apparent to one of ordinary skill in the art in light of the teachings herein. Battery (40) may be rechargeable or not, as desired. When coupled with power socket (20), battery (40) is operable to provide enough power to control module (12) and end effector (14) to perform at least part of a surgical procedure using an activated component of end effector (14).

Plug (50) of the present example is coupled with an integral cable (52), which is further removably coupled with a generator (60). Plug (50) and cable (52) may be provided as disposable components or as reusable, sterilizable components. Generator (60) may be coupled with a conventional AC wall outlet (not shown) and is operable to convert power from a conventional AC wall outlet into power suited for use in surgical instrument (10). In some versions, generator (60) comprises a G11 Generator by Ethicon Endo-Surgery, Inc. of Cincinnati, Ohio. Generator (60) may be operable to vary its power output mode based on whether surgical instrument (10) is an ultrasonic surgical instrument, an electrosurgical instrument, etc. Variations in power output mode may be manually selected by the operator; or may be automatically selected by generator (60) sensing the type of instrument that is coupled with generator (60). By way of example only, generator (60) may be constructed in accordance with at least some of the teachings of U.S. Pub. No. 2011/0015631, entitled "Ultrasonic Surgical Instruments," published Jan. 20, 2011, issued as U.S. Pat. No. 8,663,220 on Mar. 4, 2014, the disclosure of which is incorporated by reference herein; U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein; and/or U.S. Pub. No. 2011/0087256, entitled "Surgical Generator for Ultrasonic and Electrosurgical Devices," published Apr. 14, 2011, issued as U.S. Pat. No. 9,060,775 on Mar. 23, 2015, the disclosure of which is incorporated by reference herein. In the present example, generator (60) is operable to communicate electrical power through cable (52) to plug (50), to thereby power surgical instrument (10).

It should also be understood that cable (52) and plug (50) may be further operable to provide unidirectional or bidirectional communication of data and/or commands, etc. between surgical instrument (10) and generator (60). By way of example only, data may be communicated through cable (52) and plug (50) in accordance with at least some of the teachings of U.S. Pub. No. 2012/0116367, entitled "Medical Device Usage Data Processing," published May 10, 2012, issued as U.S. Pat. No. 9,095,346 on Aug. 4, 2018, the disclosure of which is incorporated by reference herein. In addition or on the alternative, such data may include software/firmware upgrades for one or more components of instruments (10); data used to provide authentication of instrument (10), plug (50), and/or generator (60); usage tracking data; auto-configuration data to tailor performance of instrument (10) based on the particular operator using instrument (10); data representing events stored on instrument (10); data captured in real time during use of instrument (10) (e.g., temperature, tissue impedance, etc.); and/or various other kinds of data. In versions where operability of instrument (10) is tailored based on the particular operator using instrument, such tailoring may be provided in accordance with at least some of the teachings of U.S. patent application Ser. No. 13/426,760, entitled "Method and Apparatus for Programming Modular Surgical Instrument," filed Mar. 22, 2012, and published Sep. 26, 2013 as U.S. Pub. No. 2013/0253499, issued as U.S. Pat. No. 9,364,249 on Jun. 14, 2016, the disclosure of which is incorporated by reference herein. It should also be understood that generator (60) may be capable of performing diagnostics on instrument (10) via cable (52) and plug (50).

In addition or in the alternative to being provided through cable (52) and plug (50), at least some of the above-described data communication functionality may be provided wirelessly between instrument (10) and generator (60); and/or between instrument (10) and some other piece of equipment. By way of example only, such wireless communication may be provided using a Bluetooth protocol, a Zigbee protocol, some other protocol, or even some other modality (e.g., non-RF wireless communication, etc.). Such wireless communication may be provided when instrument (10) is coupled with battery (40); and in some instances even when instrument (10) is coupled with plug (50) and cable (52). While the above-described example includes data communication between instrument (10) and generator (60), it should be understood that data may be communicated between instrument (10) and some other piece of equipment, wirelessly or via wire, in addition to or in lieu of being communicated between instrument (10) and generator (60). By way of example only, data may be communicated from instrument (10) to a laparoscopic camera display. Other types of equipment that instrument (10) may communicate with will be apparent to those of ordinary skill in the art in view of the teachings herein.

Generator (60) may also be capable of providing user feedback (e.g., audible tones, lights, graphical/textual messages, etc.) that instrument (10) might otherwise be incapable of providing when instrument (10) is driven by battery (40). Such user feedback at generator (60) may be driven by data received through cable (52) and plug (50). For instance, the user feedback may indicate when end effector (14) is being activated, when a cycle has completed, when a timer has run, when there is an alert condition, instructions for setup, troubleshooting, the longitudinal position of a translating knife in end effector (14), the thickness of tissue clamped between jaws of end effector (14), etc. Some versions of instrument (10) may be configured to provide user feedback through instrument itself (10). For instance, instrument (10) may provide user feedback in accordance with at least some of the teachings of U.S. Pub. No. 2012/0116364, entitled "User Feedback through Handpiece of Surgical Instrument," published May 10, 2012, issued as U.S. Pat. No. 9,364,279 on Jun. 14, 2016, the disclosure of which is incorporated by reference herein and/or U.S. Pub. No. 2012/0116267, entitled "User Feedback trough End Effector of Surgical Instrument," published May 10, 2012, issued as U.S. Pat. No. 9,526,921 on Dec. 27, 2016, the disclosure of which is incorporated by reference herein. Even in instances where instrument (10) is capable of providing user feedback on its own, such user feedback features of instrument (10) may be bypassed in favor of providing the user feedback through generator (60) when instrument (10) is coupled with generator (60) via cable (52) and plug (50). Alternatively, user feedback provided through generator (60) may supplement user feedback provided through instrument (10).

In some versions, instrument (10) communicates data (e.g., tissue impedance, other electrosurgical performance data, etc.) to generator (60) and/or to some other smart receiver; and then the generator (60) and/or other smart receiver communicates information back to instrument (10) to instruct instrument (10) to output certain user feedback. Thus, even in instances where instrument (10) itself provides user feedback, such user feedback may be driven at least in part by instructions from generator (60), with such instructions being based at least in part by data communicated from instrument (10) to generator (60). The data from instrument (10) to generator (60) and/or the user feedback commands from generator (60) to instrument (10) may be communicated via cable (52) and plug (50) and/or otherwise.

It should also be understood that instrument (10) may communicate data wirelessly to generator (60) to provide the user feedback through generator (60). Again, such wireless communication may be provided using a Bluetooth protocol, a Zigbee protocol, some other protocol, or even some other modality (e.g., non-RF wireless communication, etc.). Such wireless communication may also be provided when instrument (10) is coupled with battery (40); and in some instances even when instrument (10) is coupled with plug (50) and cable (52).

While the above-described example includes data communication between instrument (10) and generator (60) for providing user feedback, it should be understood that data may be communicated between instrument (10) and some other piece of equipment, wirelessly or via wire, in addition to or in lieu of being communicated between instrument (10) and generator (60), to provide user feedback. By way of example only, data may be communicated from instrument (10) to a laparoscopic camera display, wirelessly or via wire, such that the laparoscopic camera display may provide audible and/or visual feedback to the user based on data from instrument (10). As yet another merely illustrative variation, data from instrument (10) may be relayed from generator (60) to another piece of equipment (e.g., a laparoscopic camera display), with any suitable combination of wires or wireless technology to provide communication between links in the chain of communication. As still another merely illustrative example, data may be relayed to a server in accordance with at least some of the teachings of U.S. patent application Ser. No. 13/426,792, entitled "Surgical Instrument Usage Data Management," filed Mar. 22, 2012, and published Sep. 26, 2013 as U.S. Pub. No. 2013/0253480, now abandoned, the disclosure of which is incorporated by reference herein.

Those of ordinary skill in the art will recognize that the above-described wireless communication examples may be carried out in numerous ways. By way of example only, wireless communication may be carried out in accordance with at least some of the teachings of U.S. Pub. No. 2012/0116381, entitled "Surgical Instrument with Charging Station and Wireless Communication," published May 10, 2012, now abandoned, the disclosure of which is incorporated by reference herein; and/or U.S. Pub. No. 2012/0116365, entitled "Surgical Instrument Safety Glasses," published May 10, 2012, issued as U.S. Pat. No. 9,011,427 on Apr. 21, 2015, the disclosure of which is incorporated by reference herein. Other suitable ways in which the above-described wireless communication examples may be carried out will be apparent to those of ordinary skill in the art in view of the teachings herein.

While cable (52) and plug (50) are integral in the present example, these components may be separable in some other versions. For instance, in some versions cable (52) may comprise a conventional cable that is typically used with generator (60); and plug (50) may be provided as an adapter that cable (52) plugs into. As another merely illustrative example, cable (52) may comprise a conventional power supply cable that plugs directly into a standard AC wall outlet, with plug (50) being an adapter that removably couples with the other end of cable (52). Similarly, regardless of whether cable (52) and plug (50) are integral, the opposite end of cable (52) may include one or more removable adapters that enable cable (52) to be selectively plugged into either generator (60) or a standard AC wall outlet. For instance, the power receiving end of cable (52) may include an integral plug that is configured to plug directly into a standard AC wall outlet, and an adapter may be coupled with this plug to enable the power receiving end of cable (52) to be plugged into generator (60). Alternatively, the power receiving end of cable (52) may include an integral plug that is configured to plug directly into generator, and an adapter may be coupled with this plug to enable the power receiving end of cable (52) to be plugged into a standard AC wall outlet. In versions where cable (52) is operable to plug into a standard AC wall outlet (with or without an adapter), cable (52) and/or plug (50) may include patient isolation circuitry in order to comply with medical electrical equipment standards (e.g., standard ICE 60601-1).

As yet another merely illustrative variation, the end of cable (52) that couples directly with instrument (10) may include a plurality of plugs (50) (or adapters) to choose from, with each plug (50) (or adapter) being associated with a particular surgical modality (e.g., electrosurgery, ultrasonic surgery, surgical stapling, etc.); and/or a particular sub-modality (e.g., bipolar electrosurgery versus monopolar electrosurgery, high energy ultrasonic surgery versus low energy ultrasonic surgery, etc.). Some versions of instrument (10) may be configured to operate in more than one surgical modality and/or sub-modality. In some such versions, instrument (10) may sense the modality and/or sub-modality associated with a selected plug (50) (or adapter), and may thereby automatically configure itself to operate in that particular modality/sub-modality. Various suitable ways in which such functionality may be carried out will be apparent to those of ordinary skill in the art in view of the teachings herein. Similarly, other suitable configurations for plug (50) and cable (52), including other suitable relationships between plug (50) and cable (52), will be apparent to those of ordinary skill in the art in view of the teachings herein.

Some versions of generator (60) may include a mode where generator provides a constant AC current as an output. Instrument (10) may be configured to operate based on DC power, such that an AC output of generator (60) would need to be rectified. Plug (50) is operable to convert such AC power output from generator (60) into DC power having a profile with parameters suitable for driving surgical instrument (10). In particular, plug (50) includes a circuit (70) that provides rectification of the AC power output of generator (60) as described in greater detail below. In versions where generator (60) is capable of providing additional modes of electrical output other than a simple, constant AC current, the user may manually select the mode where generator (60) will provide the simple, constant AC current when the user couples cable (52) with generator (60). Alternatively, the end of cable (52) that plugs into generator (60) may include an EEPROM and/or other feature that is recognized by generator (60), such that generator (60) automatically selects the constant AC current output mode when cable (52) is plugged into generator (60).

Figure 2:
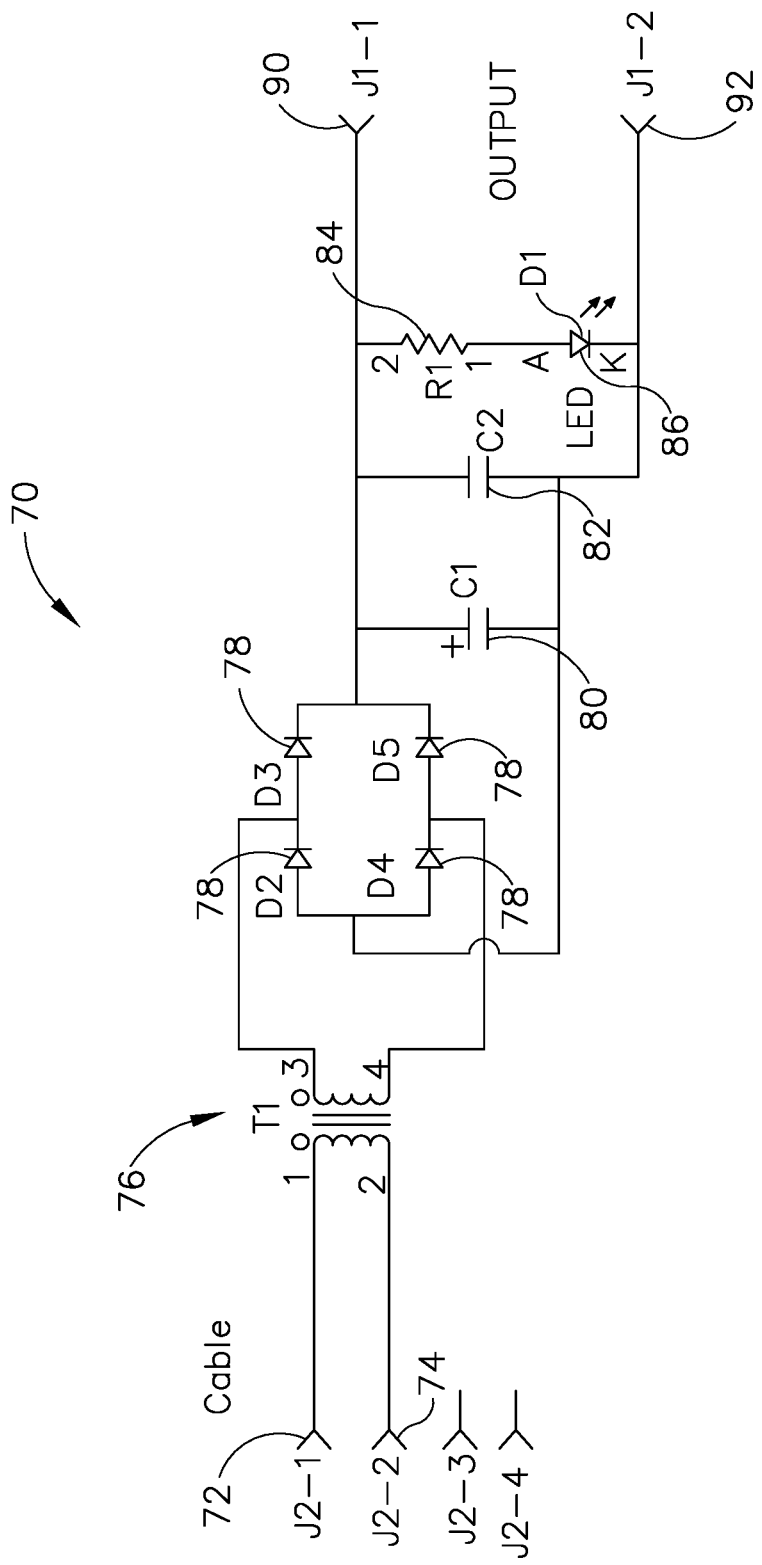
FIG. 2 depicts an electrical schematic view of exemplary circuitry that may be incorporated into the corded power source option of FIG. 1.

As shown in FIG. 2, circuit (70) of the present example includes a pair of inputs (72, 74) leading from cable (52) to a toroid transformer (76), which then leads to a set of four diodes (78). Diodes (78) are further coupled with a pair of capacitors (80, 82) in parallel, including a filter capacitor (80) and a decoupling capacitor (82). In further parallel with capacitors (80, 82) is a series including a current limiting resistor (84) and an LED (86). Circuit (70) terminates at a pair of outputs (90, 92), which are coupled with control module (12) when plug (50) is fully coupled with power socket (20). Of course, the foregoing components and arrangement for circuit (70) are merely exemplary. Various other suitable components and configurations that may be used for circuit (70) will be apparent to those of ordinary skill in the art in view of the teachings herein. Circuit (70)

of the present example provides an output of approximately 12 VDC at approximately 6 amps, though it should be understood that circuit (70) may instead output power having any other suitable power profile.

While circuit (70) is located in plug (50) in the present example, it should be understood that at least some components of circuit (70) (if not all components of circuit (70)) may be located elsewhere. By way of example only, at least some components of circuit (70) may be located in a module located anywhere along the length of cable (52). In addition or in the alternative, at least some components of circuit (70) may be located in a plug (not shown) at the opposite end of cable (52), which is received in a socket (not shown) of generator (60). In addition or in the alternative, at least some components of circuit (70) may be located in surgical instrument (10).

It should be understood that generator (60) may only provide driving power to the circuitry in plug (50) on demand, such that instrument (10) does not actually receive driving power in the absence of user input (18) being actuated. The circuitry in plug (50) and instrument (10) may nevertheless receive enough power to recognize when user input (18) is being actuated. Thus, when user input (18) is in fact actuated, the circuitry in plug (50) may send an activation signal to generator (60), which may then provide the driving power to plug (50) and instrument (10) in response to that activation signal. When the operator releases user input (18) or when circuitry otherwise recognizes an idle state, the circuitry in plug (50) may send an idle signal to generator (60), which may then return to an idle mode in response to that idle signal.

It should also be understood that circuit (70) may be modified such that cable (52) may be plugged directly into a conventional AC wall outlet, such that generator (60) may simply be omitted if desired. In other words, cable (52) and plug (50) may be capable of providing suitable power to instrument (10) by simply plugging cable (52) directly into a conventional AC wall outlet. Furthermore, circuit (70) may include one or more control modules that are operable to execute control algorithms, based on the type of instrument (10) and based on data from sensor (16), etc. For instance, such control modules may execute control algorithms that might otherwise be executed by generator (60) when generator (60) is coupled with a conventional corded version of instrument (10). Such control algorithms may automatically tune or otherwise control the power output to instrument (10), such that instrument (10) does not necessarily just receive a constant DC power signal. In addition or in the alternative, such control modules may be integrated into instrument (10).

In some instances, surgical instrument (10) comprises a surgical stapling and cutting instrument. By way of example only, surgical instrument (10) may be constructed in accordance with at least some of the teachings of U.S. Pat. No. 7,416,101; U.S. Pub. No. 2009/0209990, issued as U.S. Pat. No. 8,657,174 on Feb. 25, 2014; U.S. Pub. No. 2012/0239012 (issued as U.S. Pat. No. 8,453,914); and/or U.S. patent application Ser. No. 13/716,308, issued as U.S. Pat. No. 9,445,816 on Sep. 20, 2016. The disclosures of each of the foregoing references are incorporated by reference herein.

As another merely illustrative example, surgical instrument (10) may comprise an ultrasonic surgical instrument. By way of example only, surgical instrument (10) may be constructed in accordance with at least some of the teachings of U.S. Pat. Nos. 5,322,055; 5,873,873; 5,980,510; 6,325, 811; 6,783,524; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2010/0069940, issued as U.S. Pat. No. 9,023,071 on May 5, 2015; U.S. Pub. No. 2011/0015660 (issued as U.S. Pat. No. 8,461,744); U.S. Pub. No. 2012/0112687, issued as U.S. Pat. No. 9,381,058 on Jul. 5, 2016; U.S. Pub. No. 2012/0116265, now abandoned; and/or U.S. Pat. App. No. 61/410,603. The disclosures of each of the foregoing references are incorporated by reference herein.

As yet another merely illustrative example, surgical instrument (10) may comprise an electrosurgical instrument. By way of example only, surgical instrument (10) may be constructed in accordance with at least some of the teachings of U.S. Pat. Nos. 6,500,176; 7,112,201; 7,125,409; 7,169, 146; 7,186,253; 7,189,233; 7,220,951; 7,309,849; 7,311, 709; 7,354,440; 7,381,209; U.S. Pub. No. 2011/0087218, issued as U.S. Pat. No. 8,939,974 on Jan. 27, 2015; U.S. Pub. No. 2012/0116379, issued as U.S. Pat. No. 9,161,803 on Oct. 20, 2015; U.S. Pub. No. 2012/0078243, issued as U.S. Pat. No. 9,877,720 on Jan. 30, 2018; U.S. Pub. No. 2012/0078247, issued as U.S. Pat. No. 9,402,682 on Aug. 2, 2016; U.S. patent application Ser. No. 13/622,729 (published as U.S. Pub. No. 2013/0030428), issued as U.S. Pat. No. 9,089,327 on Jul. 28, 2015; U.S. patent application Ser. No. 13/622,735 (published as U.S. Pub. No. 2013/0023868), issued as U.S. Pat. No. 9,545,253 on Jan. 17, 2017; and/or U.S. patent application Ser. No. 13/658,784 (published as U.S. Pub. No. 2013/0103023), issued as U.S. Pat. No. 9,421,060 on Aug. 23, 2016. The disclosures of each of the foregoing references are incorporated by reference herein.

In some versions, surgical instrument (10) may provide functionalities associated with both ultrasonic surgical instruments and electrosurgical instruments. By way of example only, surgical instrument (10) may be constructed in accordance with at least some of the teachings of U.S. Pat. No. 6,251,110, entitled "Combined Radio Frequency and Ultrasonic Surgical Device," issued Jun. 26, 2001; and/or U.S. Pub. No. 2011/0015627, entitled "Impedance Monitoring Apparatus, System, and Method for Ultrasonic Surgical Instruments," published Jan. 20, 2011, issued as U.S. Pat. No. 9,017,326 on Apr. 28, 2015. The disclosures of each of the foregoing references are incorporated by reference herein. In some such versions, the additional functionalities associated with an electrosurgical instrument are only added when cable (52) and plug (50) are coupled with instrument (10), such that instrument (10) only provides ultrasonic instrument functionalities when instrument (10) is driven by battery (40). Similarly, coupling instrument (10) with cable (52) and plug (50) may alter the functionality of one or more user inputs (18), such that user inputs (18) provide responses that differ when cable (52) and plug (50) are coupled with instrument (10) (as compared to responses provided when instrument (10) is driven by battery (40)). For instance, one user input (18) that would provide an ultrasonic output function when instrument (10) is driven by battery (40) may instead provide an electrosurgical output function when cable (52) and plug (50) are coupled with instrument (10).

The following describes several merely illustrative examples of how the above teachings relating to instrument (10) may be incorporated into surgical staplers and ultrasonic surgical instruments. Other suitable examples will be apparent to those of ordinary skill in the art in view of the teachings herein. Similarly, various suitable ways in which the above teachings relating to instrument (10) may be incorporated into electrosurgical instruments will be apparent to those of ordinary skill in the art in view of the teachings herein.

A. Exemplary Surgical Stapler with Interchangeable Power Source Options

Figure 3:
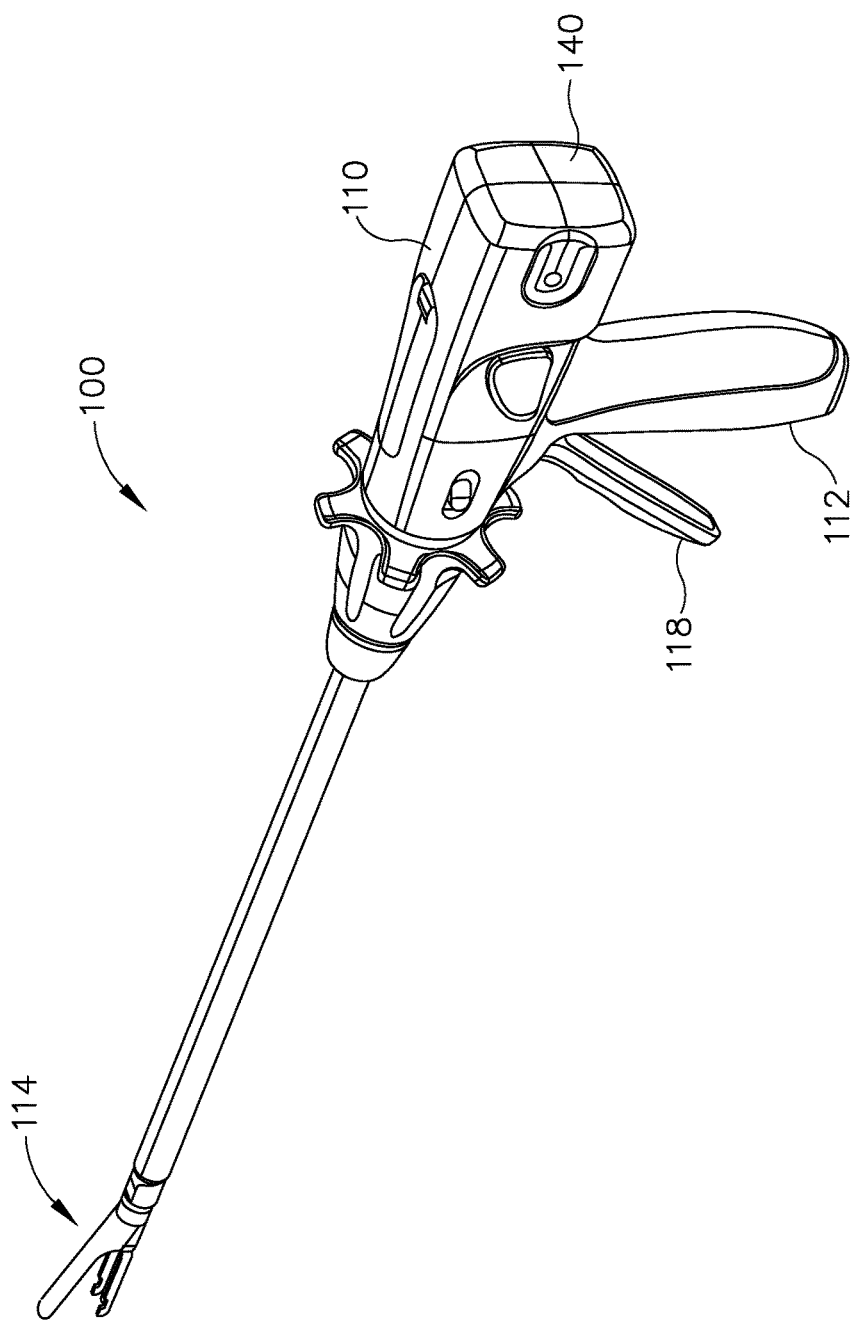
FIG. 3 depicts a perspective view of an exemplary surgical stapling instrument with a battery inserted in the handpiece.
Figure 4:
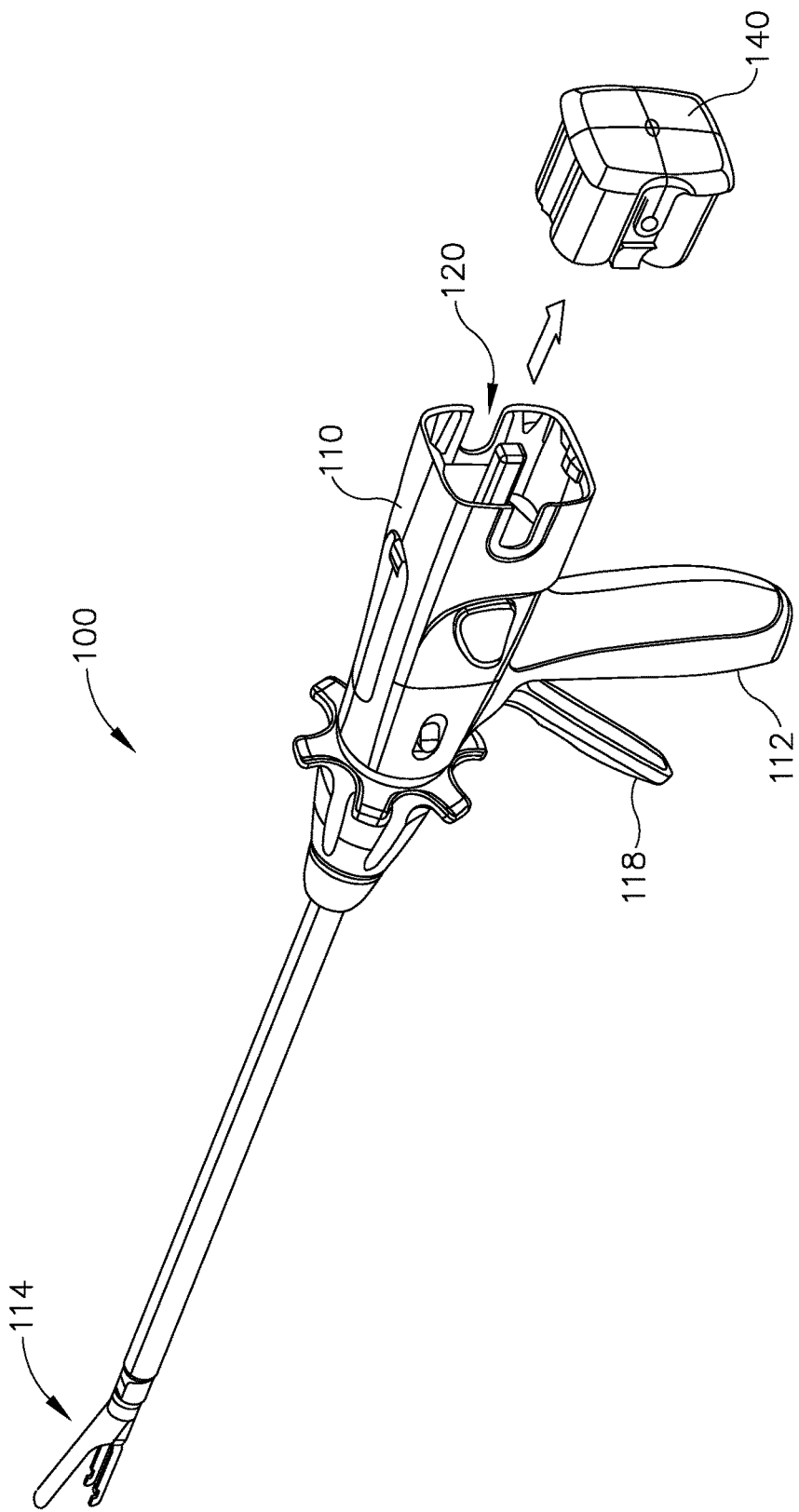
FIG. 4 depicts a perspective view of the stapling instrument of FIG. 3, with the battery removed from the handpiece.
Figure 5:
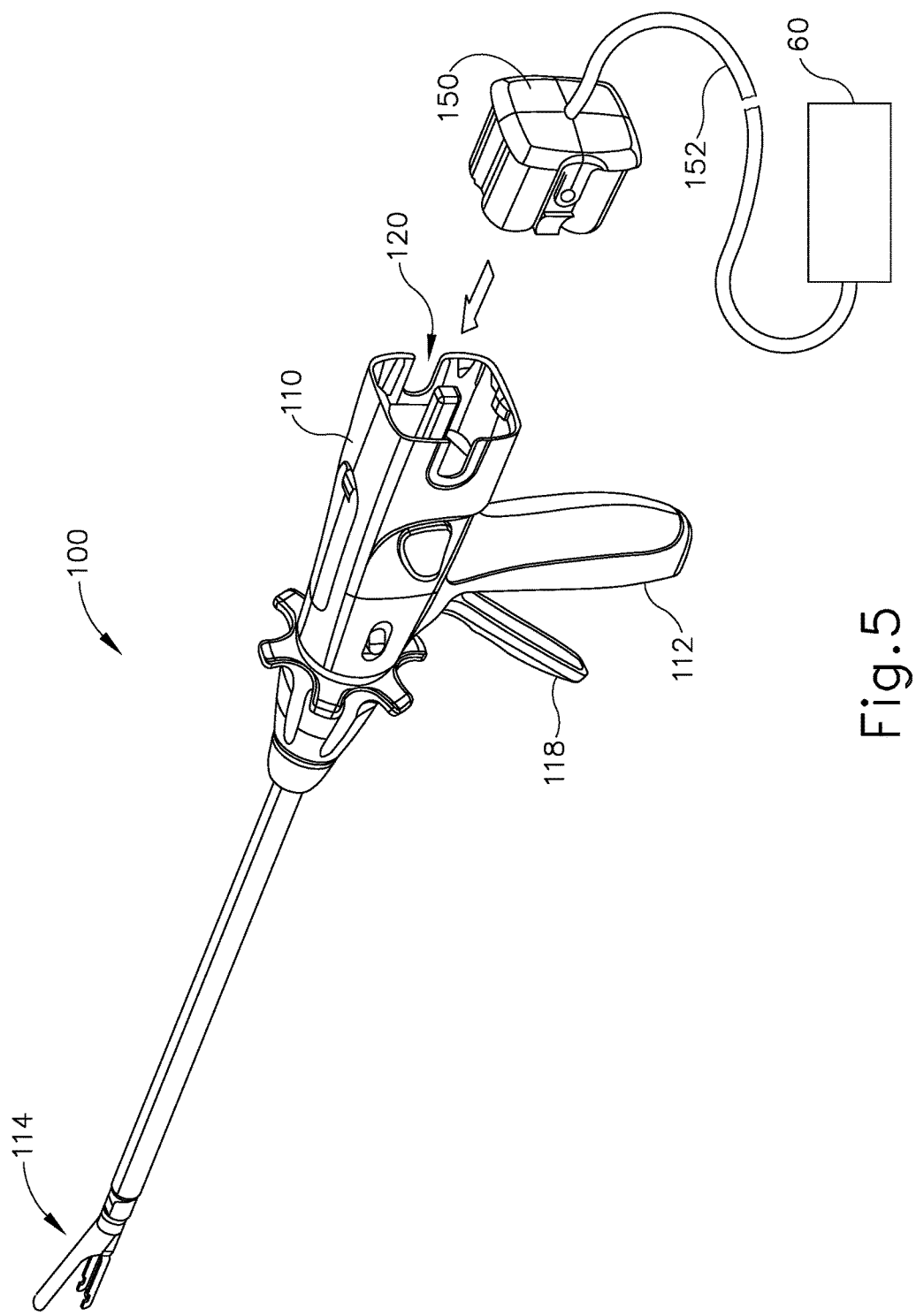
FIG. 5 depicts a perspective view of the stapling instrument of FIG. 3, with a corded power adapter positioned for insertion in the handpiece.

FIGS. 3-5 show a merely illustrative example of a form that surgical instrument (10) may take. In particular, FIGS. 3-5 show a surgical stapler (100) that includes a handpiece (110), an end effector (114), and a trigger (118) that is operable to selectively actuate end effector (114). Handpiece (110) of this example includes a pistol grip (112), though it should be understood that any other suitable configuration may be used. As shown in FIG. 3, handpiece (110) is configured to receive a battery (140). Battery (140) is operable to power a motor (not shown) in handpiece (110), which is further operable to drive end effector (114) in response to an operator squeezing trigger (118) toward pistol grip (112). By way of example only, surgical stapler (100) may be constructed and/or operable in accordance with at least some of the teachings of U.S. Pat. No. 7,416,101; U.S. Pub. No. 2009/0209990, issued as U.S. Pat. No. 8,657,174 on Feb. 25, 2014; U.S. Pub. No. 2012/0239012 (issued as U.S. Pat. No. 8,453,914); and/or U.S. patent application Ser. No. 13/716,308, issued as U.S. Pat. No. 9,445,816 on Sep. 20, 2016, the disclosures of which are incorporated by reference herein.

As shown in FIG. 4, battery (140) is selectively removable from handpiece (110), leaving an open power socket (120) at the proximal end of handpiece (110). By way of example only, one or more resiliently biased latch features may be used to selectively secure battery (140) within power socket (120). As shown in FIG. 5, a plug (150) is configured to fit in power socket (120) in place of battery (140). In particular, plug (150) of this example is sized and shaped substantially identically to battery (140); and includes the same kind of features as found in battery (140) to selectively secure plug (150) to handpiece (110). Plug (150) includes an integral cable (152), which is further coupled with generator (60). Plug (150) may include circuitry identical to circuitry (70) described above, such that plug (150) is ultimately operable to deliver the same DC power profile to surgical instrument (100) as would otherwise be delivered by battery (140), despite the communication of AC power from generator (60) to plug (150) via cable (152). It should therefore be understood that plug (150), cable (152), and generator (60) together serve as a substitute for battery (140).

In an exemplary use, an operator may initially start using stapling instrument (100) in a surgical procedure with battery (140) inserted as shown in FIG. 3. In the event that the power level of battery (140) drops below a critical level, the operator may remove battery (140) from power socket (120) as shown in FIG. 4 and then insert plug (150) into power socket (120) as shown in FIG. 5. The operator may then continue to use stapling instrument (100) in the surgical procedure. In instances where the operator expects to use stapling instrument (100) repeatedly and for an extended period of time during a particular surgical procedure, the operator may simply begin the procedure with plug (150) inserted in power socket (120), not using battery (140) at all. Other suitable ways in which stapling instrument (100) may be used with battery (140) and/or plug (150), on a selective basis, will be apparent to those of ordinary skill in the art in view of the teachings herein.

Figure 6:
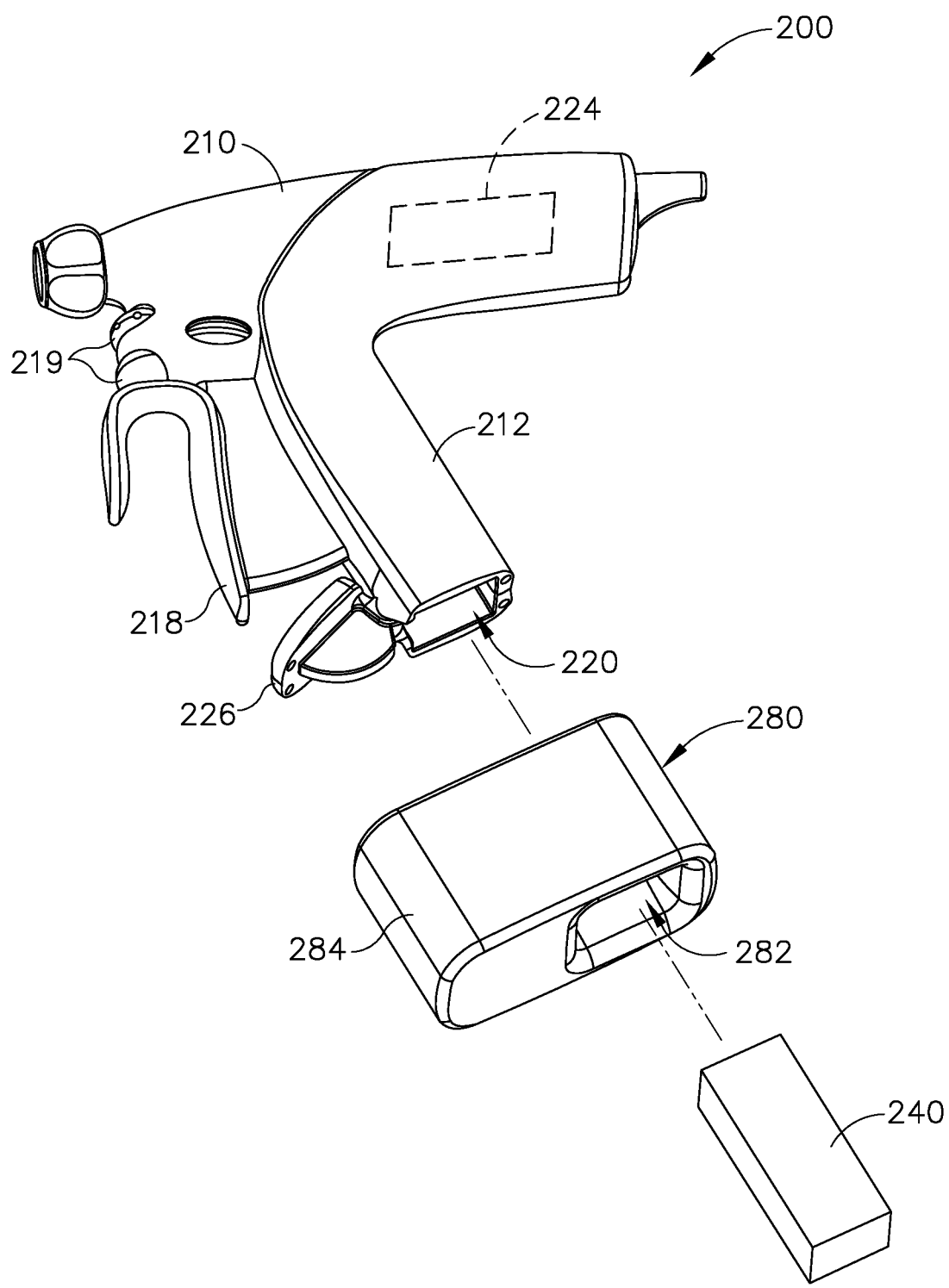
FIG. 6 depicts a perspective view of an exemplary ultrasonic surgical instrument handpiece, with a battery positioned for insertion in the handpiece via a sterile interface component.
Figure 8:
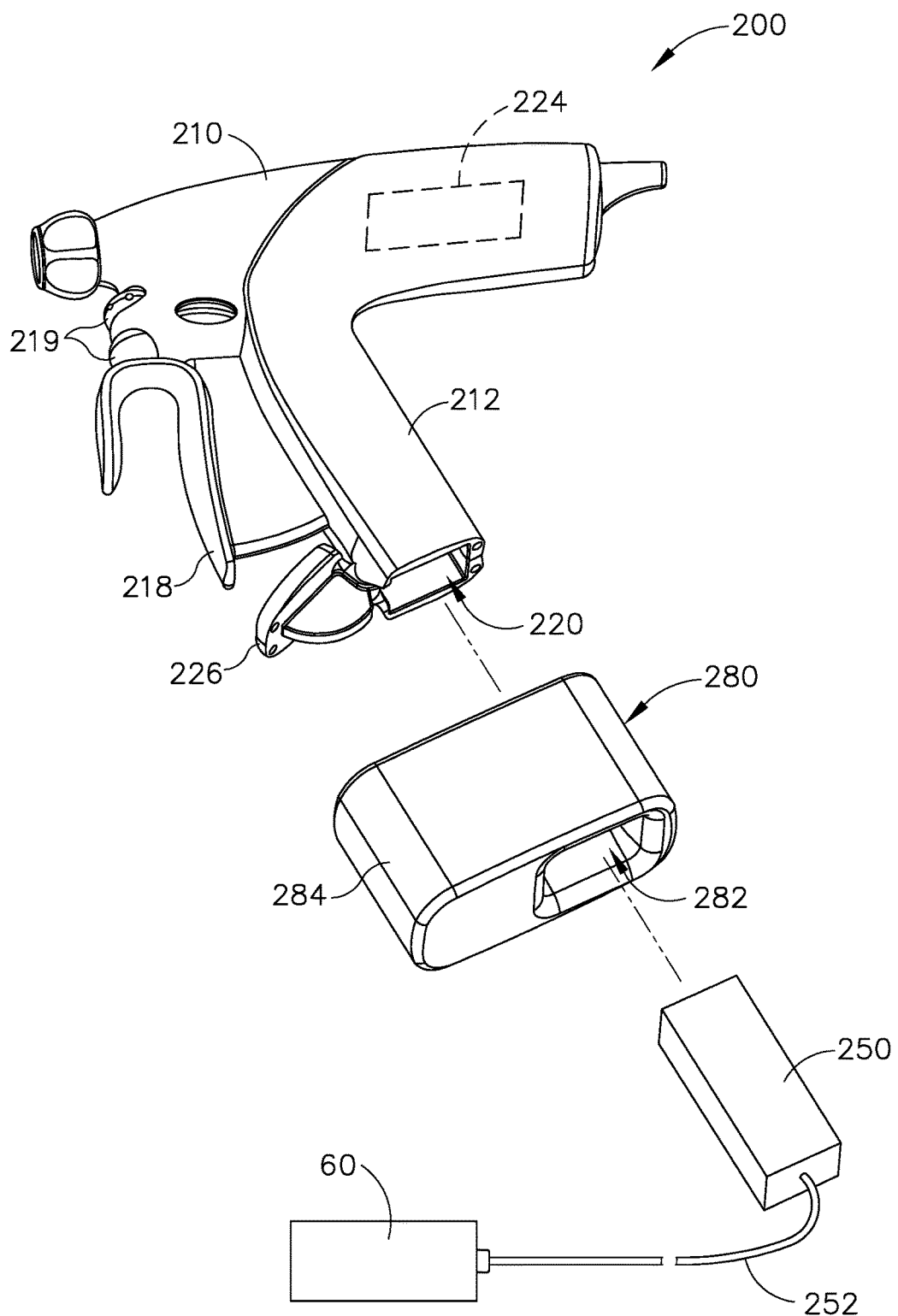
FIG. 8 depicts a perspective view of the ultrasonic surgical instrument of FIG. 6, with a corded power adapter positioned for insertion in the handpiece via the sterile interface component.

B. Exemplary Ultrasonic Surgical Instrument with Interchangeable Power Source Options FIGS. 6 and 8 show another merely illustrative example of a form that surgical instrument (10) may take. In particular, FIGS. 6 and 8 show an ultrasonic surgical instrument (200) that includes a handpiece (210), which is operable to selectively couple with a modular shaft assembly and end effector (not shown). By way of example only, such selective coupling and modularity may be provided in accordance with at least some of the teachings herein and/or at least some of the teachings of U.S. Pub. No. 2012/0116388, entitled "Surgical Instrument with Modular Shaft and End Effector," published May 10, 2012, issued as U.S. Pat. No. 9,510,895 on Dec. 6, 2016, the disclosure of which is incorporated by reference herein; U.S. Pub. No. 2012/0116394, entitled "Surgical Instrument with Pivoting Coupling to Modular Shaft and End Effector," published May 10, 2012, issued as U.S. Pat. No. 9,011,471 on Apr. 21, 2015, the disclosure of which is incorporated by reference herein; U.S. Pub. No. 2012/0116395, entitled "Surgical Instrument with Modular Shaft and Transducer," published May 10, 2012, issued as U.S. Pat. No. 9,308,009 on Apr. 12, 2016, the disclosure of which is incorporated by reference herein; U.S. Pub. No. 2012/0116260, entitled "Surgical Instrument with Motorized Attachment Feature," published May 10, 2012, issued as U.S. Pat. No. 10,085,792 on Oct. 2, 2018, the disclosure of which is incorporated by reference herein; U.S. Pub. No. 2012/0116363, entitled "Surgical Instrument Handpiece with Resiliently Biased Coupling to Modular Shaft and End Effector," published May 10, 2012, issued as U.S. Pat. No. 9,375,255 on Jun. 28, 2016, the disclosure of which is incorporated by reference herein; U.S. Pub. No. 2012/0116389, entitled "Surgical Instrument Shaft with Resiliently Biased Coupling to Handpiece," published May 10, 2012, issued as U.S. Pat. No. 9,421,062 on Aug. 23, 2016, the disclosure of which is incorporated by reference herein; U.S. Pub. No. 2012/0116396, entitled "Surgical Instrument with Modular End Effector," published May 10, 2012, issued as U.S. Pat. No. 8,998,939 on Apr. 7, 2015, the disclosure of which is incorporated by reference herein; U.S. Pub. No. 2012/0116266, entitled "Surgical Instrument with Modular End Effector and Detection Feature," published May 10, 2012, now abandoned, the disclosure of which is incorporated by reference herein; U.S. patent application Ser. No. 13/269,899, entitled "Ultrasonic Surgical Instrument with Modular End Effector," filed Oct. 10, 2011, and published as U.S. Pub. No. 2013/0090577 on Apr. 11, 2013, issued as U.S. Pat. No. 9,050,125 on Jun. 9, 2015, the disclosure of which is incorporated by reference herein; U.S. patent application Ser. No. 13/426,760, entitled "Method and Apparatus for Programming Modular Surgical Instrument," filed Mar. 22, 2012, issued as U.S. Pat. No. 9,364,249 on Jun. 14, 2016, the disclosure of which is incorporated by reference herein; and/or U.S. patent application Ser. No. 13/484,547, entitled "Loading Cartridge for Surgical Instrument End Effector," filed May 31, 2012, issued as U.S. Pat. No. 9,301,772 on Apr. 5, 2016, the disclosure of which is incorporated by reference herein. Other suitable ways in which handpiece (210) may selectively couple with a shaft assembly and end effector will be apparent to those of ordinary skill in the art in view of the teachings herein.

Handpiece (210) of the present example includes a pistol grip (212), a trigger (218), and buttons (219). Trigger (218) is operable to mechanically drive a clamping feature of an end effector at the distal end of a shaft assembly coupled with handpiece (210). Buttons (219) are operable to selectively activate an ultrasonic transducer (224) within handpiece (210), to thereby drive an ultrasonic blade of an end effector at the distal end of a shaft assembly coupled with handpiece (210). Pistol grip (212) defines a power socket (220) that is configured to receive a battery (240). Pistol grip (212) further includes a pivoting door (226) that is operable to fully close battery (240) within power socket (220). Battery (240) is operable to power ultrasonic transducer (224) in handpiece (210), to thereby drive an ultrasonic blade of an end effector at the distal end of a shaft assembly coupled with handpiece (210) when buttons (219) are depressed by the operator. By way of example only, when a shaft assembly and end effector are coupled with handpiece (210), ultrasonic surgical instrument (200) may be constructed and/or operable in accordance with at least some of the teachings of U.S. Pat. Nos. 5,322,055; 5,873,873; 5,980,510; 6,325,811; 6,783,524; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2010/0069940, issued as U.S. Pat. No. 9,023,071 on May 5, 2015; U.S. Pub. No. 2011/0015660 (issued as U.S. Pat. No. 8,461,744); U.S. Pub. No. 2012/0112687, issued as U.S. Pat. No. 9,381,058 on Jul. 5, 2016; U.S. Pub. No. 2012/0116265, now abandoned; and/or U.S. Pat. App. No. 61/410,603, the disclosures of which are incorporated by reference herein.

Figure 7:
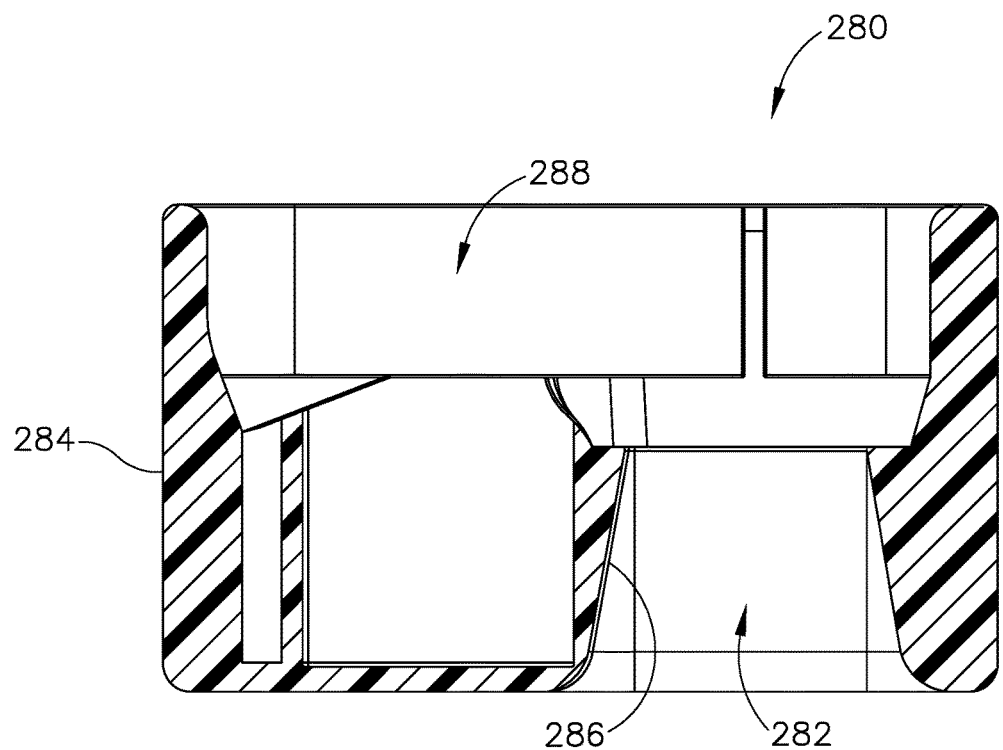
FIG. 7 depicts a side cross-sectional view of the sterile interface component of FIG. 6.

In the present example, a battery guide (280) is used to guide battery (240) into power socket (220). Battery guide (280) includes a passageway (282) through which battery (240) may be passed and an outer wall (284) that may be grasped by a clinician to hold battery guide (280) in position against the bottom of pistol grip (212). As best seen in FIG. 7, passageway (282) is defined by an inner wall (286) that is angled to assist in receiving and guiding battery (240) into alignment with power socket (220). As also seen in FIG. 7, battery guide (280) includes an inner recess configured to accommodate pivoting door (226) in the open position when battery guide (280) is held against the bottom of pistol grip (212). Other suitable configurations for battery guide (280) will be apparent to those of ordinary skill in the art in view of the teachings herein.

It should also be understood that battery guide (280) may be used as a sterile barrier between battery (240) and the exterior of handpiece (210). In particular, in some instances handpiece (210) and battery guide (280) are sterile while battery (240) is not sterile. One or more clinicians with sterile hands may hold battery guide (280) against the bottom of pistol grip (212). A clinician with non-sterile hands may then insert battery (240) through passage (282) and into power socket (220). The clinician with sterile hands may then close door (226) behind battery (240). Thus, the hands of this clinician remain sterile, and battery (240) has not compromised the sterility of handpiece (210) because battery guide (280) has served as a guide to position battery (240) directly into power socket (220). Battery guide (280) may be disposed of after a single use; or may be sterilized for subsequent use. Of course, battery guide (280) is merely optional and may simply be omitted if desired. By way of example only, battery (240) may be handled in accordance with at least some of the teachings one or more of the following: U.S. Pub. No. 2012/0115005, entitled "Power Source Management for Medical Device," published May 10, 2012, issued as U.S. Pat. No. 9,017,849 on Apr. 28, 2015, the disclosure of which is incorporated by reference herein; U.S. Pub. No. 2012/0110810, entitled "Medical Device with Feature for Sterile Acceptance of Non-Sterile Reusable Component," published May 10, 2012, issued as U.S. Pat. No. 9,072,523 on Jul. 7, 2015, the disclosure of which is incorporated by reference herein; and/or U.S. Pub. No. 2012/0112687, entitled "Recharge System for Medical Devices," published May 10, 2012, issued as U.S. Pat. No. 9,381,058 on Jul. 5, 2016, the disclosure of which is incorporated by reference herein.

As shown in FIG. 8, a plug (250) is configured to fit through passage (282) and into power socket (220) in place of battery (240). In particular, plug (250) of this example is sized and shaped substantially identically to battery (240). Plug (250) includes an integral cable (252), which is further coupled with generator (60). Plug (250) may include circuitry identical to circuitry (70) described above, such that plug (250) is ultimately operable to deliver the same DC power profile to surgical instrument (200) as would otherwise be delivered by battery (240), despite the communication of AC power from generator (60) to plug (250) via cable (252). It should therefore be understood that plug (250), cable (252), and generator (60) together serve as a substitute for battery (240).

In an exemplary use, an operator may initially start using ultrasonic surgical instrument (200) in a surgical procedure with battery (240) inserted in power socket (220). In the event that the power level of battery (240) drops below a critical level, the operator may remove battery (240) from power socket (220) and then insert plug (250) into power socket (220) via guide (280) as shown in FIG. 8. The operator may then continue to use ultrasonic surgical instrument (200) in the surgical procedure. In instances where the operator expects to use ultrasonic surgical instrument (200) repeatedly and for an extended period of time during a particular surgical procedure, the operator may simply begin the procedure with plug (250) inserted in power socket (220), not using battery (240) at all. Other suitable ways in which ultrasonic surgical instrument (200) may be used with battery (240) and/or plug (250), on a selective basis, will be apparent to those of ordinary skill in the art in view of the teachings herein.

Figure 9:
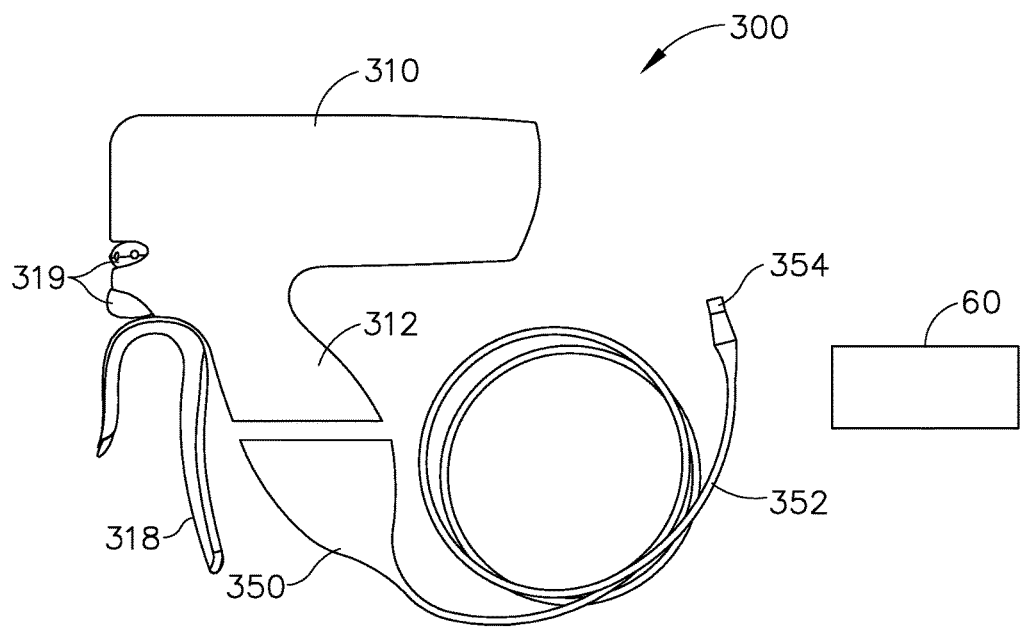
FIG. 9 depicts a side view of another exemplary ultrasonic surgical instrument handpiece, including a removable grip portion.

FIG. 9 shows another merely illustrative example of an ultrasonic surgical instrument (300) that may serve as a variation of surgical instrument (10). In this example, ultrasonic surgical instrument (300) comprises a handpiece (310) that is operable to selectively couple with a modular shaft assembly and end effector (not shown), similar to handpiece (210) described above. Handpiece (310) of the present example includes a partial pistol grip (312), a trigger (318), and buttons (319). Trigger (318) and buttons (319) of this example are substantially identical to trigger (218) and buttons (219) described above.

Partial pistol grip (312) is configured to couple with a plug (350), which defines the remaining portion of a full pistol grip with partial pistol grip (312). Thus, when an operator grasps handpiece (310), the operator will grasp both partial pistol grip (312) and plug (350). Partial pistol grip (312) may alternatively couple with a battery (not shown) that defines the remaining portion of a full pistol grip with partial pistol grip (312), such that an operator will grasp both partial pistol grip (312) and the battery when the operator grasps handpiece (310). Plug (350) includes an integral cable (352), which terminates in a generator plug (354) that couples with generator (60). Plug (350) may include circuitry identical to circuitry (70) described above, such that plug (350) is ultimately operable to deliver the same DC power profile to surgical instrument (300) as would otherwise be delivered by a battery, despite the communication of AC power from generator (60) to plug (350) via cable (352). It should therefore be understood that plug (350), cable (352), and generator (60) together serve as a substitute for a battery.

Figure 10:
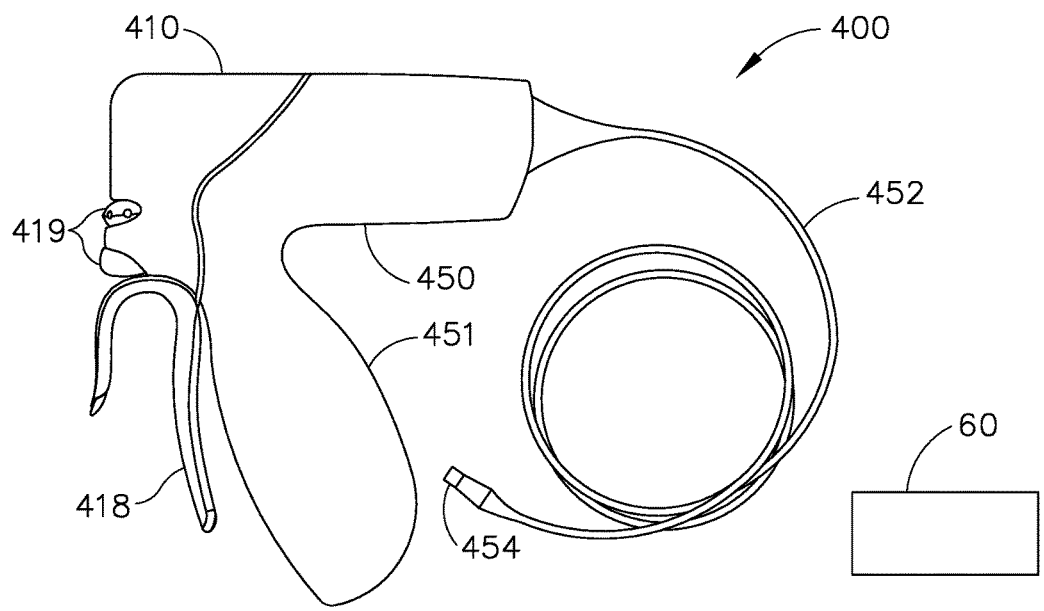
FIG. 10 depicts a side view of yet another exemplary ultrasonic surgical instrument handpiece including a removable grip portion.

FIG. 10 shows yet another merely illustrative example of an ultrasonic surgical instrument (400) that may serve as a variation of surgical instrument (10). In this example, ultrasonic surgical instrument (400) comprises a handpiece (410) that is operable to selectively couple with a modular shaft assembly and end effector (not shown), similar to handpiece (210) described above. Handpiece (410) of the present example includes a trigger (418) and buttons (419). Trigger (418) and buttons (419) of this example are substantially identical to trigger (218) and buttons (219) described above.

Handpiece (410) is configured to couple with a plug (450), which defines the remaining portion of handpiece (410) including a pistol grip (451). Thus, when an operator grasps handpiece (410), the operator will grasp plug (450). Handpiece (410) may alternatively couple with a battery (not shown) that defines a pistol grip, such that the operator will grasp the battery when the operator grasps handpiece (410). Plug (450) includes an integral cable (452), which terminates in a generator plug (454) that couples with generator (60). Plug (450) may include circuitry identical to circuitry (70) described above, such that plug (450) is ultimately operable to deliver the same DC power profile to surgical instrument (400) as would otherwise be delivered by a battery, despite the communication of AC power from generator (60) to plug (450) via cable (452). It should therefore be understood that plug (450), cable (452), and generator (60) together serve as a substitute for a battery.

Still other suitable ways in which the principals of instrument (10) may be applied to surgical stapling instruments, ultrasonic surgical instruments, electrosurgical instruments, and various other kinds of instruments will be apparent to those of ordinary skill in the art in view of the teachings herein.

Figure 11:
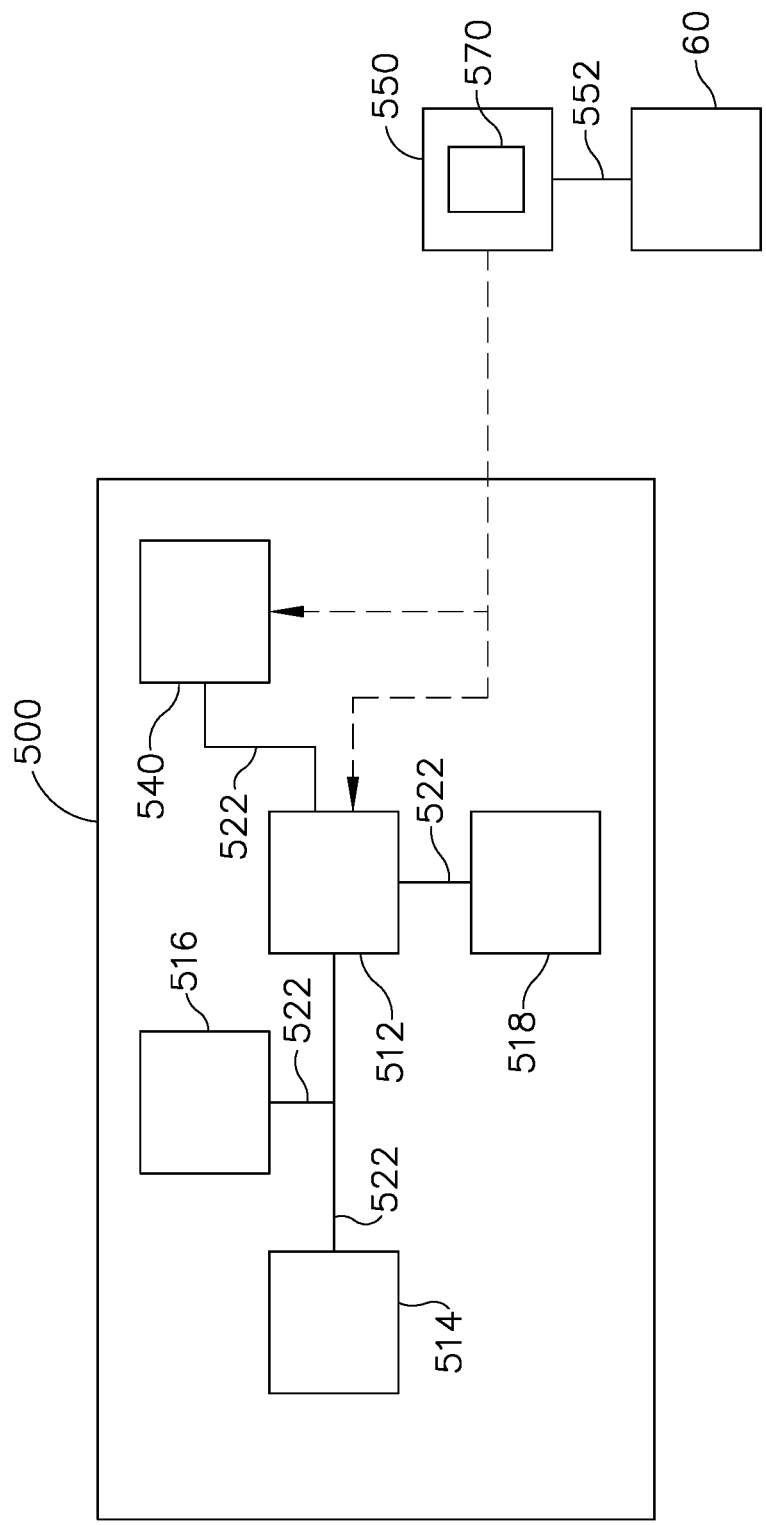
FIG. 11 depicts a block schematic view of an exemplary surgical instrument with an integral power source and a supplemental power cord.

II. Exemplary Surgical Instrument with Integral Power Source Supplemental Power Cord In some instances, an instrument operator either cannot remove a battery from an instrument during a surgical procedure or simply does not wish to remove a battery from an instrument during a surgical procedure. For instance, when the power level of a battery falls below an acceptable level, the operator may wish to quickly transition to corded power to avoid switching out the battery or waiting to recharge the battery. This may be due to perceived time constraints, due to sterility concerns, or due to the battery being either non-removable or relatively difficult to remove. It may therefore be desirable in some instances to provide an instrument that is capable of at least initially running on battery powered; but may selectively run on corded power without having to remove the battery from the instrument. In instances where the operator would simply prefer to provide power from a cord rather than from a battery, regardless of the power level present in the battery, it may be desirable to enable the operator to select corded power over battery power at the operator's whim. FIG. 11 shows an exemplary surgical instrument (500) that is capable of operating on battery power or corded power, without requiring removal of the battery in order to operate on corded power.

Surgical instrument (500) of this example is substantially similar to surgical instrument (10) in many respects. For instance, surgical instrument (500) of this example includes a control module (512), an end effector (514), a sensor (516), a user input (518), and an integral battery (540). End effector (514), sensor (516), user input (518), and battery (540) are all in communication with control module (512) via wires (522). Control module (512) is thus operable to receive inputs (e.g., power, data, etc.) from end effector (514), sensor (516), user input (518), and/or battery (540); and to drive end effector (514) based on one or more control algorithms and based on input received from sensor (516) and/or user input (518). Control module (512) may comprise a microprocessor, an application specific integrated circuit (ASIC), memory, a printed circuit board (PCB), a storage device (such as a solid state drive or hard disk), firmware, software, and/or various other suitable components as will be apparent to those of ordinary skill in the art in view of the teachings herein. Wires (522) may comprise any suitable conventional wiring, traces in rigid circuit boards or flexible circuits, and/or any other suitable components that are operable to communicate electrical power and/or data/signals.

End effector (514) may include a variety of features that are operable to manipulate tissue. By way of example only, end effector (514) may include one or more movable jaws that are operable to grasp tissue, a tissue cutting feature (e.g., translating knife blade), a set of staples and staple drivers operable to sever tissue, an ultrasonic blade operable to denature proteins in tissue by applying ultrasonic energy to the tissue, one or more electrodes operable to provide RF energy (e.g., bipolar or monopolar) to tissue, and/or any other suitable features as will be apparent to those of ordinary skill in the art in view of the teachings herein. End effector (514) of this example comprises an active feature, such as an ultrasonic blade, a pair of clamping jaws, a sharp knife, a staple driving assembly, a monopolar RF electrode, a pair of bipolar RF electrodes, a thermal heating element, and/or various other components that may be driven by electrical power. In some instances, end effector (514) is removable from the rest of surgical instrument (500) for servicing, testing, replacement, or any other purpose as will be apparent to one of ordinary skill in the art in view of the teachings herein. It should also be understood that surgical instrument (500) may be configured to accept various kinds of end effectors (514) to perform different kinds of activities. For instance, surgical instrument (500) may accept a removable stapling end effector (514), which may be removed and replaced with an electrosurgical end effector (514), which may be removed and replaced with an ultrasonic end effector (514), and so on.

Sensor (516) of the present example is operable to provide a variety of information to control module (512) during a procedure. By way of example only, such configurations may include sensing a temperature at end effector (514) or determining the oscillation rate of end effector (514). Data from sensor (516) may be processed by control module (512) to effect the delivery of power to end effector (514) (e.g., in a feedback loop, etc.). Various other configurations of sensor (516) may be provided depending upon the purpose of surgical instrument (500) as will be apparent to those of ordinary skill in the art in view of the teachings herein. Various suitable uses for sensor (516) and various forms that sensor (516) may take will be apparent to those of ordinary skill in the art in view of the teachings herein. Of course, as with other components described herein, surgical instrument (500) may have more than one sensor (516); or sensor (516) may simply be omitted if desired.

Trigger (518) may be configured to selectively provide power from a power source (540, 560) to end effector (514) (and/or to some other component of surgical instrument (500)) to activate surgical instrument (500) when performing a procedure. By way of example only, trigger (518) may comprise one or more pushbuttons, one or more pivoting triggers, one or more sliders, one or more knobs, and/or variations and combinations thereof. Other suitable forms that trigger (518) may take will be apparent to those of ordinary skill in the art in view of the teachings herein.

In the present example, battery (540) is fully integrated into surgical instrument (500) such that battery (540) is not removable from surgical instrument (500) (e.g., at least not without destroying instrument (500)). In some other examples, battery (540) is removable from surgical instrument (500). For instance, surgical instrument (500) may have a socket similar to power socket (20) described above. Other suitable configurations will be apparent to those of ordinary skill in the art in view of the teachings herein. Battery (540) may comprise a pack of one or more NiMH batteries, Li-ion batteries (e.g., prismatic cell type lithium ion batteries, etc.), Ni-Cad batteries, or any other type of portable power source as may be apparent to one of ordinary skill in the art in light of the teachings herein. Battery (540) may be rechargeable or not, as desired. Battery (540) is operable to provide enough power to control module (512) and end effector (514) to perform at least part of a surgical procedure.

Plug (550) of the present example is coupled with an integral cable (552), which is further removably coupled with the same kind of generator (60) described above. Generator (60) is operable to communicate electrical power through cable (552) to plug (550), to thereby power surgical instrument (500). It should also be understood that cable (552) and plug (50) may be further operable to provide unidirectional or bidirectional communication of data and/or commands, etc. between surgical instrument (500) and generator (60), just like the communication described above with respect to instrument (10). Similarly, instrument (500) may be capable of providing wireless communication with generator (60) and/or with other equipment, just like the wireless communication described above with respect to instrument (10). Plug (550) also includes a circuit (570) that is substantially identical to circuit (70) described above, such that plug (550) is operable to rectify AC power from generator (60) to provide DC power to instrument (500).

As shown, plug (550) is operable to couple with control module (512) and/or battery (540). In some versions, plug (550) is received in a socket that is wired directly to control module (512). Alternatively, plug (550) may be received in a socket that is wired directly to battery (540). As yet another merely illustrative example, plug (550) may be received in a socket that is wired directly to both control module (512) and battery (540). In some versions, when plug (550) is coupled with instrument (500), battery (540) is bypassed through common switching, such that plug (550) provides full operational power to instrument (500). It should be understood that, in addition to providing full operational power to instrument (500), such that instrument (500) is fully operable from electrical power provided through plug (550), plug (550) may also be operable to charge battery (540) when plug (550) is coupled with instrument (500). Plug (550), cable (552), and generator (60) may thus collectively serve dual roles as primary electrical power source for instrument (500) and as recharging equipment for battery (540). In some versions, these two roles may be served simultaneously. In some other versions, plug (550), cable (552), and generator (60) only serve the role of recharger when plug (550), cable (552), and generator (60) are not actively being used to serve as primary electrical power source for instrument (500). For instance, plug (550), cable (552), and generator (60) may serve a role as recharger for battery (540) when end effector (514) is idle. As another merely illustrative example, plug (550), cable (552), and generator (60) may serve a role as recharger for battery (540) in accordance with at least some of the teachings of U.S. Pub. No. 2012/0116380, entitled "Sterile Medical Instrument Charging Device," published May 10, 2012, issued as U.S. Pat. No. 9,597,143 on Mar. 21, 2017, the disclosure of which is incorporated by reference herein. Even in versions where generator (60) is operable to provide recharging capabilities via cable (552) and plug (550), cable (552) may be configured to plug into a separate recharging device (e.g., to free up generator (60) for some other use after surgical instrument (500) is done being used in a surgical procedure, etc.). Of course, some versions of battery (540) may be non-rechargeable, such that plug (550), cable (552), and generator (60) serve only as a substitute power source and/or supplemental power source for operation of instrument (500), without also providing some kind of recharging functionality. Other suitable configurations and operabilities will be apparent to those of ordinary skill in the art in view of the teachings herein.

In some instances, surgical instrument (500) comprises a surgical stapling and cutting instrument. By way of example only, surgical instrument (500) may be constructed in accordance with at least some of the teachings of U.S. Pat. No. 7,416,101; U.S. Pub. No. 2009/0209990, issued as U.S. Pat. No. 8,657,174 on Feb. 25, 2014; U.S. Pub. No. 2012/0239012 (issued as U.S. Pat. No. 8,453,914); and/or U.S. patent application Ser. No. 13/716,308, issued as U.S. Pat. No. 9,445,816 on Sep. 20, 2016. The disclosures of each of the foregoing references are incorporated by reference herein.

As another merely illustrative example, surgical instrument (500) may comprise an ultrasonic surgical instrument. By way of example only, surgical instrument (500) may be constructed in accordance with at least some of the teachings of U.S. Pat. Nos. 5,322,055; 5,873,873; 5,980,510; 6,325,811; 6,783,524; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2010/0069940, issued as U.S. Pat. No. 9,023,071 May 5, 2015; U.S. Pub. No. 2011/0015660 (issued as U.S. Pat. No. 8,461,744); U.S. Pub. No. 2012/0112687, issued as U.S. Pat. No. 9,381,058 on Jul. 5, 2016; U.S. Pub. No. 2012/0116265, now abandoned; and/or U.S. Pat. App. No. 61/410,603. The disclosures of each of the foregoing references are incorporated by reference herein.

Figure 12:
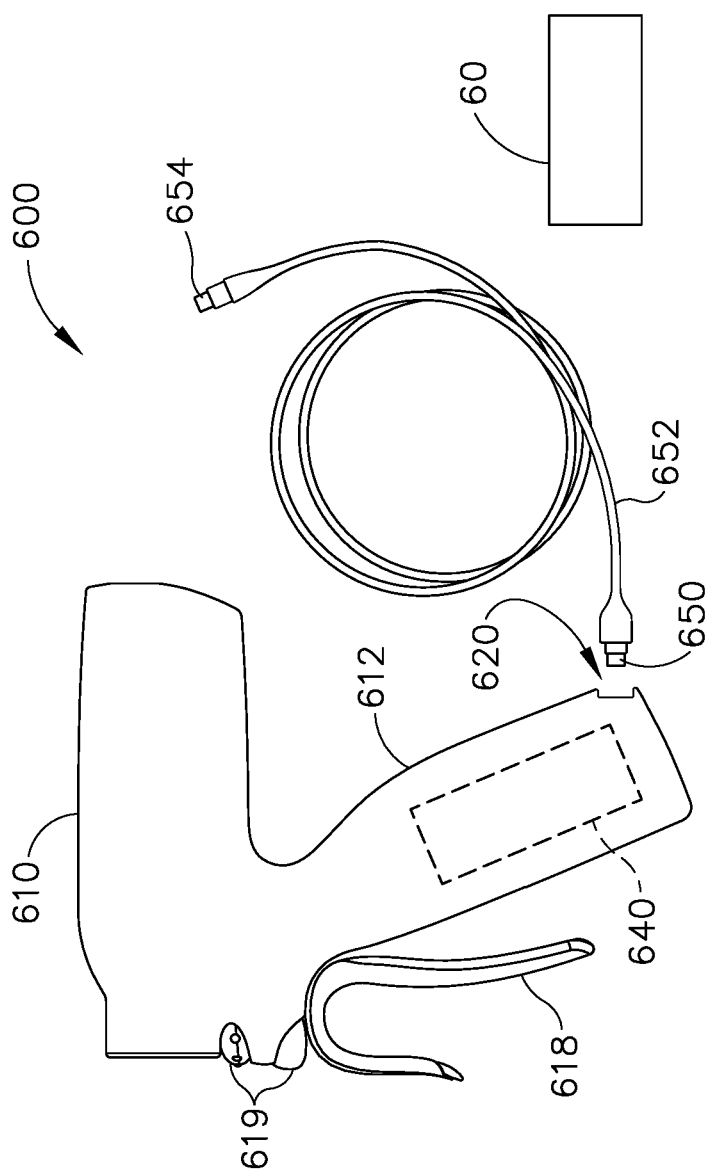
FIG. 12 depicts a side view of an exemplary ultrasonic surgical instrument handpiece, including an integral power source and a supplemental power cord positioned for coupling with the handpiece.

FIG. 12 shows a merely illustrative example of a form that surgical instrument (500) may take in an ultrasonic surgical instrument (600). In this example, ultrasonic surgical instrument (600) comprises a handpiece (610) that is operable to selectively couple with a modular shaft assembly and end effector (not shown), similar to handpiece (210) described above. Handpiece (610) of the present example includes a pistol grip (612), a trigger (618), and buttons (619). Trigger (618) and buttons (619) of this example are substantially identical to trigger (218) and buttons (219) described above. Pistol grip (612) houses an integral battery (640) in this example. Pistol grip (612) includes a socket (620) that is operable to receive a plug (650). Plug (650) includes an integral cable (652), which terminates in a generator plug (654) that couples with generator (60). Plug (650) may include circuitry identical to circuitry (70) described above, such that plug (650) is ultimately operable to deliver the same DC power profile to surgical instrument (600) as would otherwise be delivered by battery (640), despite the communication of AC power from generator (60) to plug (650) via cable (652). It should therefore be understood that plug (650), cable (652), and generator (60) may together serve as a substitute for battery (640). In addition or in the alternative, plug (650), cable (652), and generator (60) may together serve as a recharger for battery (640).

As yet another merely illustrative example, surgical instrument (500) may comprise an electrosurgical instrument. By way of example only, surgical instrument (500) may be constructed in accordance with at least some of the teachings of U.S. Pat. Nos. 6,500,176; 7,112,201; 7,125,409; 7,169,146; 7,186,253; 7,189,233; 7,220,951; 7,309,849; 7,311,709; 7,354,440; 7,381,209; U.S. Pub. No. 2011/0087218, issued as U.S. Pat. No. 8,939,974 on Jan. 27, 2015; U.S. Pub. No. 2012/0116379, issued as U.S. Pat. No. 9,161,803 on Oct. 20, 2015; U.S. Pub. No. 2012/0078243, issued as U.S. Pat. No. 9,877,720 on Jan. 30, 2018; U.S. Pub. No. 2012/0078247; issued as U.S. Pat. No. 9,402,682 on Aug. 2, 2016; U.S. patent application Ser. No. 13/622,729 (published as U.S. Pub. No. 2013/0030428), issued as U.S. Pat. No. 9,089,327 on Jul. 28, 2015; U.S. patent application Ser. No. 13/622,735 (published as U.S. Pub. No. 2013/0023868), issued as U.S. Pat. No. 9,545,253 on Jan. 17, 2017; and/or U.S. patent application Ser. No. 13/658,784 (published as U.S. Pub. No. 2013/0103023), issued as U.S. Pat. No. 9,421,060 on Aug. 23, 2016. The disclosures of each of the foregoing references are incorporated by reference herein.

In some versions, surgical instrument (500) may provide functionalities associated with both ultrasonic surgical instruments and electrosurgical instruments. By way of example only, surgical instrument (500) may be constructed in accordance with at least some of the teachings of U.S. Pat. No. 6,251,110, entitled "Combined Radio Frequency and Ultrasonic Surgical Device," issued Jun. 26, 2001; and/or U.S. Pub. No. 2011/0015627, entitled "Impedance Monitoring Apparatus, System, and Method for Ultrasonic Surgical Instruments," published Jan. 20, 2011, issued as U.S. Pat. No. 9,017,326 on Apr. 28, 2015. The disclosures of each of the foregoing references are incorporated by reference herein. In some such versions, the additional functionalities associated with an electrosurgical instrument are only added when cable (552) and plug (550) are coupled with instrument (500), such that instrument (500) only provides ultrasonic instrument functionalities when instrument (500) is driven solely by battery (540). Similarly, coupling instrument (500) with cable (552) and plug (550) may alter the functionality of one or more user inputs (518), such that user inputs (518) provide responses that differ when cable (552) and plug (550) are coupled with instrument (500) (as compared to responses provided when instrument (500) is driven solely by battery (540)). For instance, one user input (518) that would provide an ultrasonic output function when instrument (500) is driven solely by battery (540) may instead provide an electrosurgical output function when cable (552) and plug (550) are coupled with instrument (500).

Still other suitable ways in which the principals of instrument (500) may be applied to surgical stapling instruments, ultrasonic surgical instruments, electrosurgical instruments, and various other kinds of instruments will be apparent to those of ordinary skill in the art in view of the teachings herein.

III. Exemplary Alternative Plug Assembly

Figure 13:
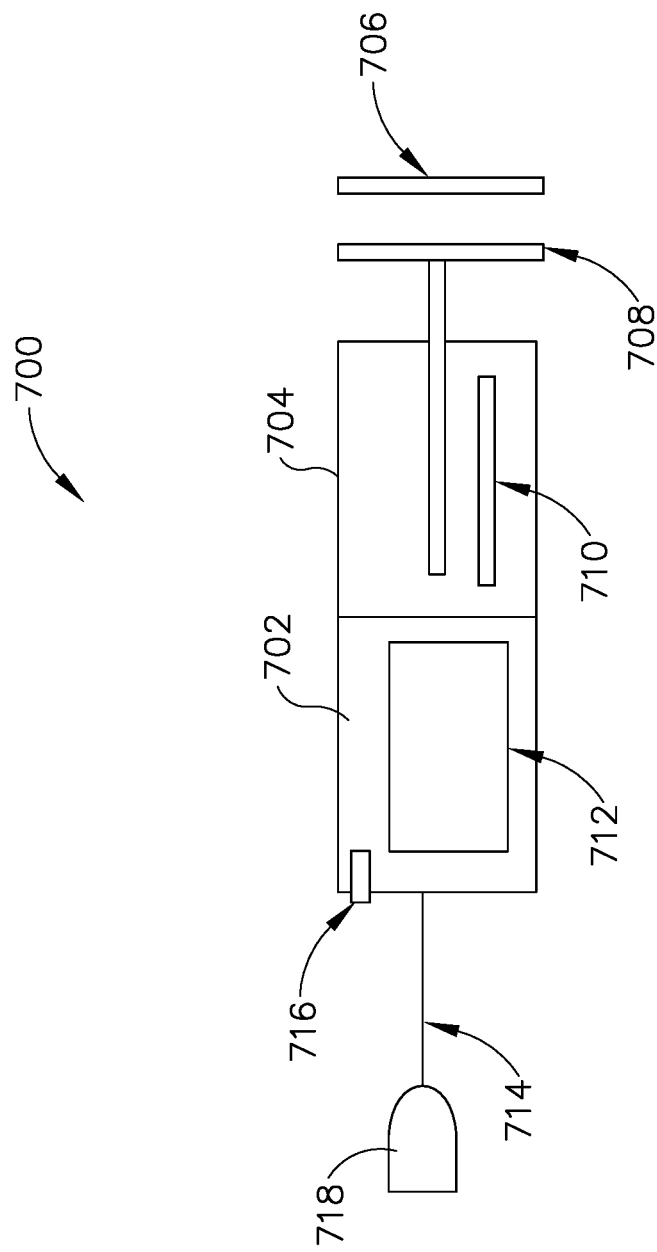
FIG. 13 depicts a block schematic view of an exemplary alternative plug assembly.

FIG. 13 depicts an exemplary alternative plug assembly (700) that may be used in place of plugs (50, 500) described above. Other than as described below, it should be understood that plug assembly (700) may be configured and/or operable in accordance with the teachings above regarding plugs (50, 500). Plug assembly (700) of this example comprises a first plug housing (702) joined with a second plug housing (704). In some other versions, a single plug housing is used instead. Plug housing (704) of the present example is configured similar to the housing of battery (40), such that plug housing (704) is removably received in socket (20) just like battery (40). Plug housing (702) is also configured similar to the housing of battery (40), though this is of course optional. A restraint feature (706) removably secures plug assembly (700) relative to instrument (10). By way of example only, restraint feature (706) may comprise a resilient latch, a clip, a clamp, and/or any other suitable structure. A contact and support feature (708) provides structural support for plug assembly (700) relative to instrument (10); and electrical continuity with instrument (10). Various suitable forms that contact and support feature (708) may take will be apparent to those of ordinary skill in the art in view of the teachings herein.

Plug housing (704) also contains a printed circuit board (710), which is in electrical communication with contact and support feature (708). Plug housing (702) contains a transformer (712), which is in electrical communication with printed circuit board (710). Transformer (712) may be configured similar to transformer (76) described above. In some versions, printed circuit board (710) includes components similar to the remaining components of circuit (70) described above. It should therefore be understood that plug assembly (700) may include the same components as circuit (70) described above and/or other components as will be apparent to those of ordinary skill in the art in view of the teachings herein. It should also be understood that such components may be allocated among either housing (702, 704) as desired.

A cable (714) extends from housing (702) and is in electrical communication with transformer (76). A plug (718) is located at the opposite end of cable (714), and is configured to plug into a corresponding socket of generator (60). An LED indicator (716) is also positioned on housing (702) in this example. LED indicator (716) is operable to selectively illuminate to indicate an operational state of plug assembly (700). By way of example only, LED indicator (716) may illuminate to indicate successful coupling between generator (60) and instrument (10). In addition or in the alternative, LED indicator (716) may flash to indicate delivery of power to tissue via end effector (14). LED indicator (716) may provide numerous flashing patterns to indicate numerous operational conditions, fault conditions, etc. Similarly, LED indicator (716) may illuminate in different colors to indicate different conditions. Various suitable forms of user feedback that may be provided through LED indicator (716) will be apparent to those of ordinary skill in the art in view of the teachings herein. Similarly, other suitable kinds of features that may be used in addition to or in lieu of LED indicator (716) to provide audio and/or visual feedback to a user will be apparent to those of ordinary skill in the art in view of the teachings herein.

IV. Exemplary Surgical Instrument with Modular Shaft Assembly

Any of the versions of surgical instrument (10) described herein (or other versions of surgical instrument (10)) may be configured to have a modular end effector or shaft assembly. For instance, surgical instrument (10) may have a handpiece or other kind of body that removably receives various kinds of shaft assemblies. Such various kinds of shaft assemblies may include those having tissue stapling features, ultrasonic blades, RF energy electrodes, surgical clip applying features, etc., such that the selection of shaft assemblies presents options for a surgeon to operate with various surgical modalities using the same handpiece. The handpiece may include features that are operable to drive the various kinds of end effectors of shaft assemblies. In some instances, shaft assemblies may be interchanged among the same handpiece during the same surgical procedure. It should also be understood that, if desired, a handpiece may be provided as a reusable component while the shaft assembly is provided as a disposable component.

Various examples of surgical instruments that have modular end effectors or shaft assemblies are described in U.S. Pub. No. 2012/0116388, issued as U.S. Pat. No. 9,510,895 on Dec. 6, 2016, the disclosure of which is incorporated by reference herein; U.S. Pub. No. 2012/0116394, issued as U.S. Pat. No. 9,011,471 on Apr. 21, 2015, the disclosure of which is incorporated by reference herein; U.S. Pub. No. 2012/0116395, issued as U.S. Pat. No. 9,308,009 on Apr. 12, 2016, the disclosure of which is incorporated by reference herein; U.S. Pub. No. 2012/0116260, issued as U.S. Pat. No. 10,085,792 on Oct. 2, 2018, the disclosure of which is incorporated by reference herein; U.S. Pub. No. 2012/0116363, issued as U.S. Pat. No. 9,375,255 on Jun. 28, 2016, the disclosure of which is incorporated by reference herein; U.S. Pub. No. 2012/0116389, issued as U.S. Pat. No. 9,421,062 on Aug. 23, 2016, the disclosure of which is incorporated by reference herein; U.S. Pub. No. 2012/0116396, issued as U.S. Pat. No. 8,998,939 on Apr. 7, 2015, the disclosure of which is incorporated by reference herein; U.S. Pub. No. 2012/0116266, now abandoned, the disclosure of which is incorporated by reference herein; U.S. patent application Ser. No. 13/269,899 (published as U.S. Pub. No. 2013/0090577), issued as U.S. Pat. No. 9,050,125 on Jun. 9, 2015, the disclosure of which is incorporated by reference herein; U.S. patent application Ser. No. 13/426,760, issued as U.S. Pat. No. 9,364,249 on Jun. 14, 2016, the disclosure of which is incorporated by reference herein; and/or U.S. patent application Ser. No. 13/484,547, issued as U.S. Pat. No. 9,301,772 on Apr. 5, 2016, the disclosure of which is incorporated by reference herein. Further examples of how surgical instrument (10) may incorporate a modular end shaft assembly will be described in greater detail below; while additional examples will be apparent to those of ordinary skill in the art in view of the teachings herein. It should be understood that the teachings below may be readily combined with any other teachings herein and/or various teachings in the numerous references that are cited herein.

Figure 14:
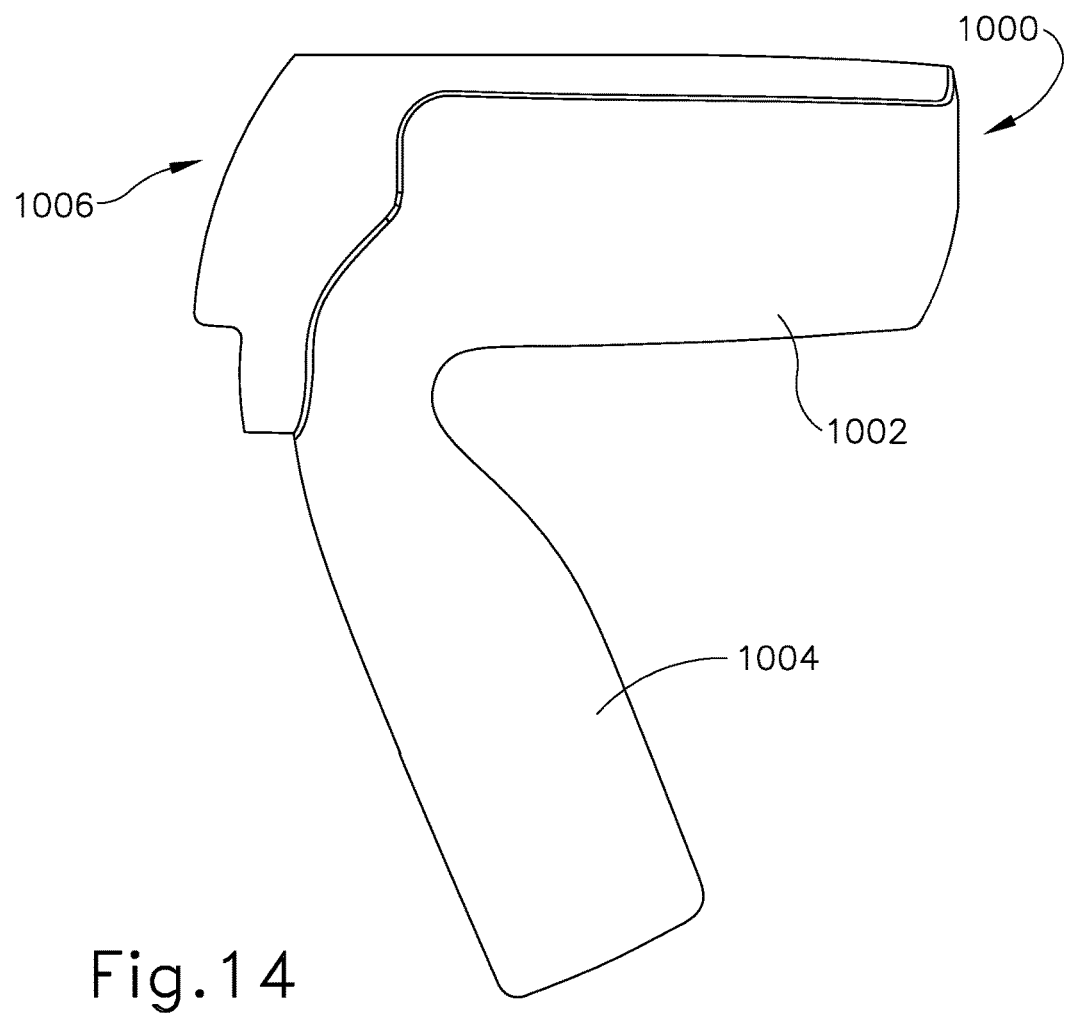
FIG. 14 depicts a side elevational view of an exemplary handpiece configured to receive a modular shaft assembly.

FIG. 14 shows an exemplary handpiece (1000) that is configured to couple with various exemplary shaft assemblies, including but not limited to shaft assemblies (1100, 1200, 1300) described below. Handpiece (1000) includes a housing (1002) that defines a pistol grip (1004) and a shaft socket (1006). While a pistol grip (1004) is provided by handpiece (1000) in this example, it should be understood that any other suitable kind of grip may be provided. Shaft socket (1006) is configured to receive a complementary control interface feature of a shaft assembly. Handpiece (1000) also includes various drive features that are operable to drive a shaft assembly via shaft socket (1006), such as electrical drive features (e.g., wires, battery, etc.), ultrasonic drive features (e.g., ultrasonic transducer, etc.), mechanical drive features (e.g., gears, motors, etc.), etc. However, in the present example, handpiece (1000) does not include user input features that are operable to activate drive features in handpiece (1000). Instead, those drive features are provided by the shaft assemblies that are coupled with handpiece (1000). This may avoid the prospect of having unused control features on handpiece (1000) and may promote acceptance of shaft assemblies that have user input features that are not yet contemplated.

Figure 15:
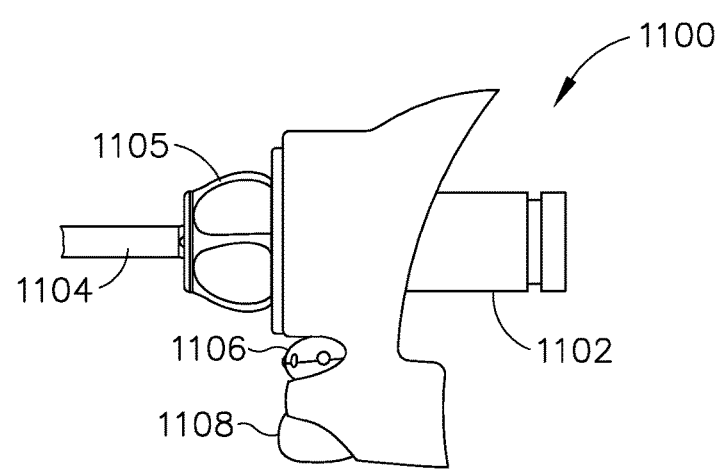
FIG. 15 depicts a side elevational view of an exemplary shaft assembly configured to couple with the handpiece of FIG. 14.

FIG. 15 shows one merely exemplary shaft assembly (1100) that may be removably coupled with handpiece (1000). Shaft assembly (1100) comprises a control interface feature (1102) that is configured for receipt in socket (1006) of handpiece (1000). Shaft assembly (1100) also includes a distally extending shaft (1104) and an optional knob (1105) that is operable to rotate shaft (1104). An end effector (not shown) at the distal end of shaft (1104) may include numerous components, including but not limited to a stapling assembly, an ultrasonic blade, RF electrodes, etc. Components of the end effector may be driven by the drive features within handpiece (1000), with the electrical/acoustic/mechanical/etc. actuation being communicated through socket (1006), control interface feature (1102), and shaft (1104).

Shaft assembly (1100) of this example also includes a first activation button (1106) and a second activation button (1008). Activation buttons (1106, 1108) are positioned for engagement by fingers of the same hand that grasps pistol grip (1004). Activation buttons (1106, 1108) are operable to selectively activate drive features in handpiece (1000). By way of example only, activation button (1106) may activate handpiece (1000) to drive an ultrasonic blade at the distal end of shaft (1104) at a high power level; while activation button (1108) may activate handpiece to drive the same ultrasonic blade at a low power level. Other suitable responses that may be triggered by activation buttons (1106, 1108) will be apparent to those of ordinary skill in the art in view of the teachings herein.

Figure 16:
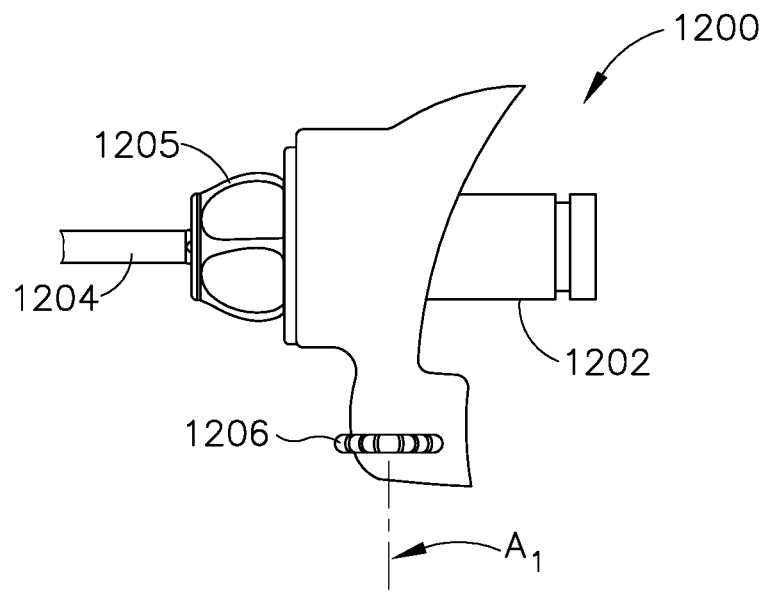
FIG. 16 depicts a side elevational view of another exemplary shaft assembly configured to couple with the handpiece of FIG. 14.

FIG. 16 shows another exemplary shaft assembly (1200) that may be removably coupled with handpiece (1000). Shaft assembly (1200) comprises a control interface feature (1202) that is configured for receipt in socket (1006) of handpiece (1000). Shaft assembly (1200) also includes a distally extending shaft (1204) and an optional knob (1205) that is operable to rotate shaft (1204). An end effector (not shown) at the distal end of shaft (1204) may include numerous components, including but not limited to a stapling assembly, an ultrasonic blade, RF electrodes, etc. Components of the end effector may be driven by the drive features within handpiece (1000), with the electrical/acoustic/mechanical/etc. actuation being communicated through socket (1006), control interface feature (1202), and shaft (1204).

Shaft assembly (1200) of this example also includes a control dial (1206) that is rotatable about an axis $(A_1)$. Control dial (1206) is positioned for engagement by fingers of the same hand that grasps pistol grip (1004). Control dial (1206) is operable to selectively activate drive features in handpiece (1000). By way of example only, shaft (1204) may include an articulation section that is operable to selectively deflect the end effector laterally away from the longitudinal axis of shaft (1204). Handpiece (1000) may include a drive feature that is operable to drive such articulation in response to rotation of control dial (1206). Other suitable responses that may be triggered by control dial (1206) will be apparent to those of ordinary skill in the art in view of the teachings herein.

Figure 17:
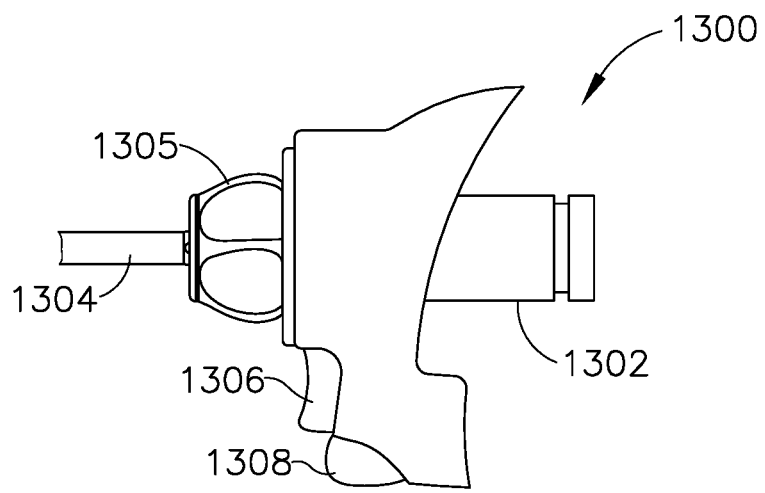
FIG. 17 depicts a side elevational view of another exemplary shaft assembly configured to couple with the handpiece of FIG. 14.

FIG. 17 shows another exemplary shaft assembly (1300) that may be removably coupled with handpiece (1000). Shaft assembly (1300) comprises a control interface feature (1302) that is configured for receipt in socket (1006) of handpiece (1000). Shaft assembly (1300) also includes a distally extending shaft (1304) and an optional knob (1305) that is operable to rotate shaft (1304). An end effector (not shown) at the distal end of shaft (1304) may include numerous components, including but not limited to a stapling assembly, an ultrasonic blade, RF electrodes, etc. Components of the end effector may be driven by the drive features within handpiece (1000), with the electrical/acoustic/mechanical/etc. actuation being communicated through socket (1006), control interface feature (1302), and shaft (1304).

Shaft assembly (1300) of this example also includes a pivoting trigger (1306) and an activation button (1308). Trigger (1306) and button (1308) are operable to selectively activate drive features in handpiece (1000). By way of example only, the end effector at the distal end of shaft (1304) may include clamping jaws and RF electrodes that are operable to apply bipolar RF energy to tissue clamped between the jaws. In some such versions, trigger (1306) may activate handpiece (1000) to drive the jaws to a closed position; while button (1308) may activate handpiece (1000) to provide RF energy to the electrodes of the jaws. Other suitable responses that may be triggered by trigger (1306) and activation button (1308) will be apparent to those of ordinary skill in the art in view of the teachings herein.

Figure 18:
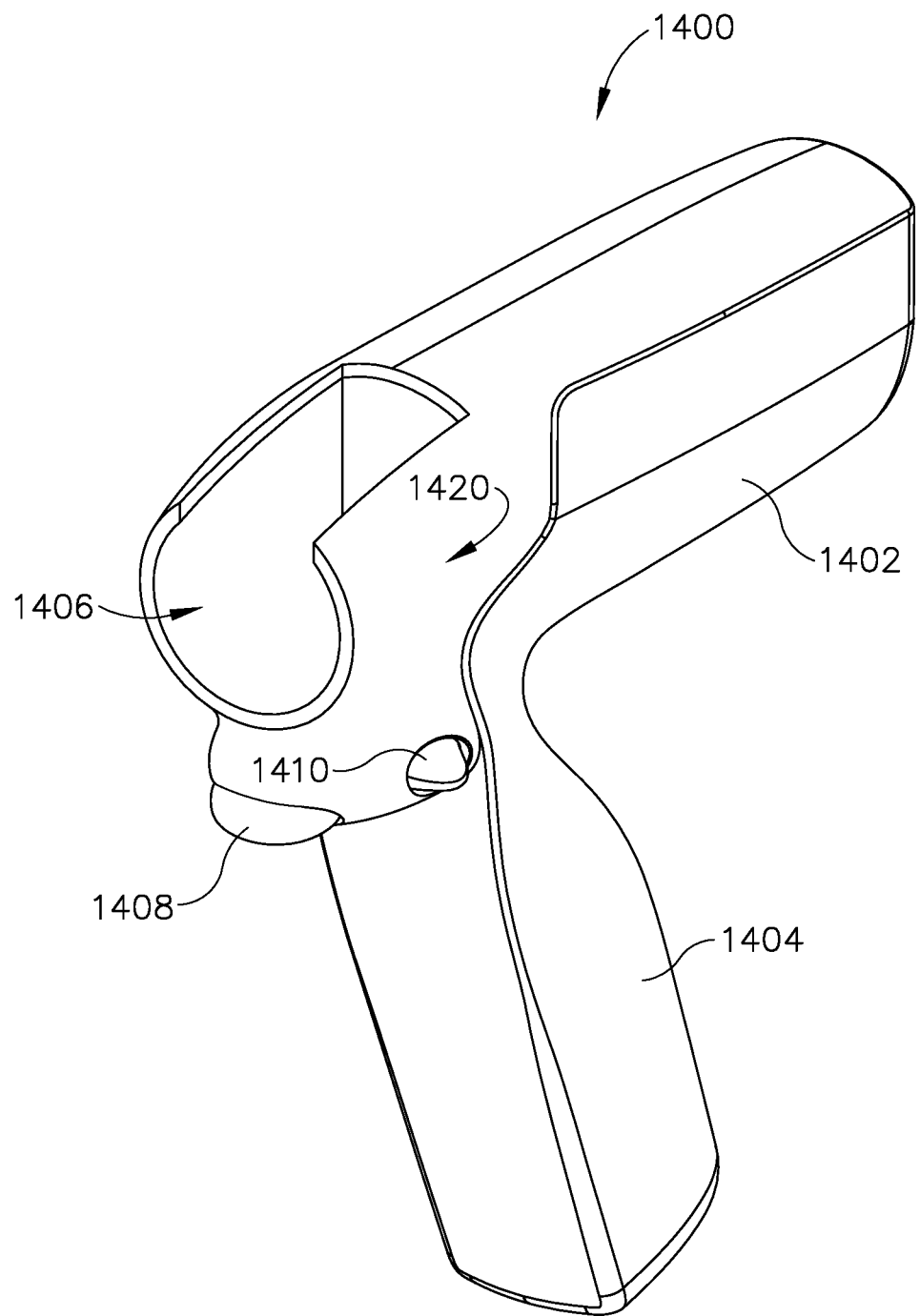
FIG. 18 depicts a side elevational view of another exemplary handpiece configured to receive a modular shaft assembly.

FIG. 18 shows another exemplary handpiece (1400) that is configured to couple with various exemplary shaft assemblies, including but not limited to shaft assemblies (1500, 1600) described below. Handpiece (1400) includes a housing (1402) that defines a pistol grip (1404) and a shaft socket (1406). While a pistol grip (1404) is provided by handpiece (1400) in this example, it should be understood that any other suitable kind of grip may be provided. Shaft socket (1406) is configured to receive a complementary control interface feature of a shaft assembly. Handpiece (1400) also includes various drive features that are operable to drive a shaft assembly via shaft socket (1406), such as electrical drive features (e.g., wires, battery, etc.), ultrasonic drive features (e.g., ultrasonic transducer, etc.), mechanical drive features (e.g., gears, motors, etc.), etc. In addition, handpiece (1400) includes a first activation button (1408) and a second activation button (1410), each of which are operable to selectively activate corresponding drive features in handpiece (1400). Handpiece (1400) of this example also includes a control zone (1420) associated with control inputs of attached shaft assemblies. Providing such a consistent location for control inputs of an attached shaft assembly may make operation of the instrument more intuitive and familiar for an operator. Of course, the designation of a control zone (1420) is merely optional.

Figure 19:
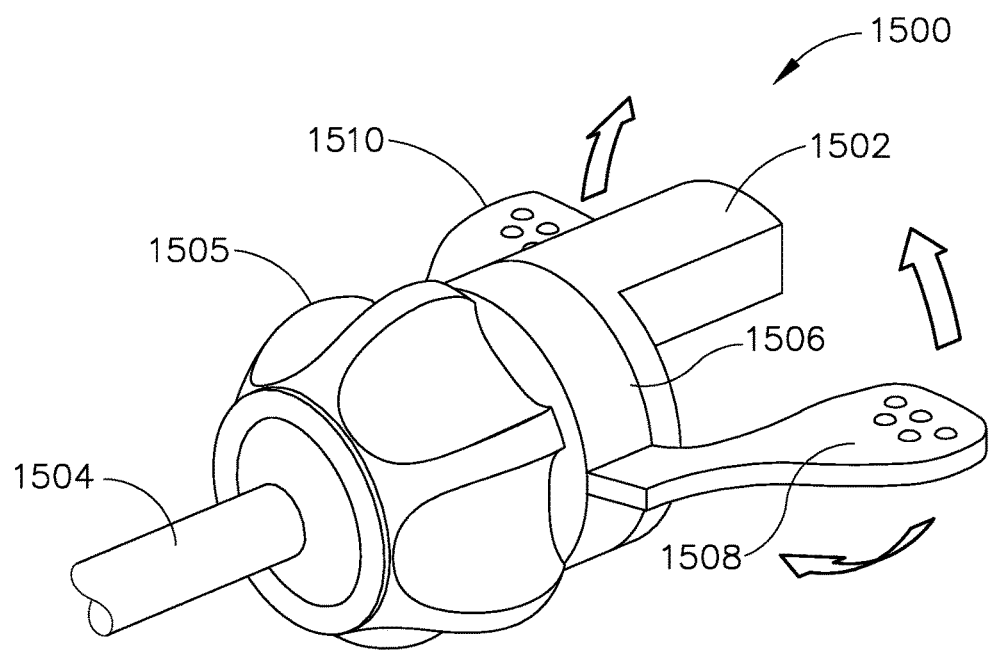
FIG. 19 depicts a perspective view of an exemplary shaft assembly configured to couple with the handpiece of FIG. 18.

FIG. 19 shows one merely exemplary shaft assembly (1500) that may be removably coupled with handpiece (1400). Shaft assembly (1500) comprises a control interface feature (1502) that is configured for receipt in socket (1406) of handpiece (1000). Shaft assembly (1500) also includes a distally extending shaft (1504) and an optional knob (1505) that is operable to rotate shaft (1504). An end effector (not shown) at the distal end of shaft (1504) may include numerous components, including but not limited to a stapling assembly, an ultrasonic blade, RF electrodes, etc. Components of the end effector may be driven by the drive features within handpiece (1400), with the electrical/acoustic/mechanical/etc. actuation being communicated through socket (1406), control interface feature (1502), and shaft (1504).

In the present example, shaft (1504) also includes an articulation section that is operable to selectively deflect the end effector laterally away from the longitudinal axis of shaft (1504). This articulation is controlled by a ring (1506) of shaft assembly (1500). Ring (1506) includes a first laterally extending paddle (1508) and a second laterally extending paddle (1510). Ring (1506) is rotatable about the longitudinal axis of shaft (1504) to activate articulation. In particular, when ring (1506) is rotated in a first angular direction about the longitudinal axis of shaft (1504) (e.g. clockwise), a drive feature in handpiece (1400) drives the end effector to deflect in a first lateral direction away from the longitudinal axis of shaft (1504) (e.g., to the right). When ring (1506) is rotated in the opposite angular direction about the longitudinal axis of shaft (1504)(e.g., counterclockwise), a drive feature in handpiece (1400) drives the end effector to deflect in a second lateral direction away from the longitudinal axis of shaft (1504)(e.g., to the left). Paddles (1508, 1510) are positioned at control zone (1420), such that the operator may use paddles (1508, 1510) to rotate ring (1506) using the same hand that grasps pistol grip (1404). Other suitable responses that may be triggered by ring (1506) will be apparent to those of ordinary skill in the art in view of the teachings herein.

Figure 20:
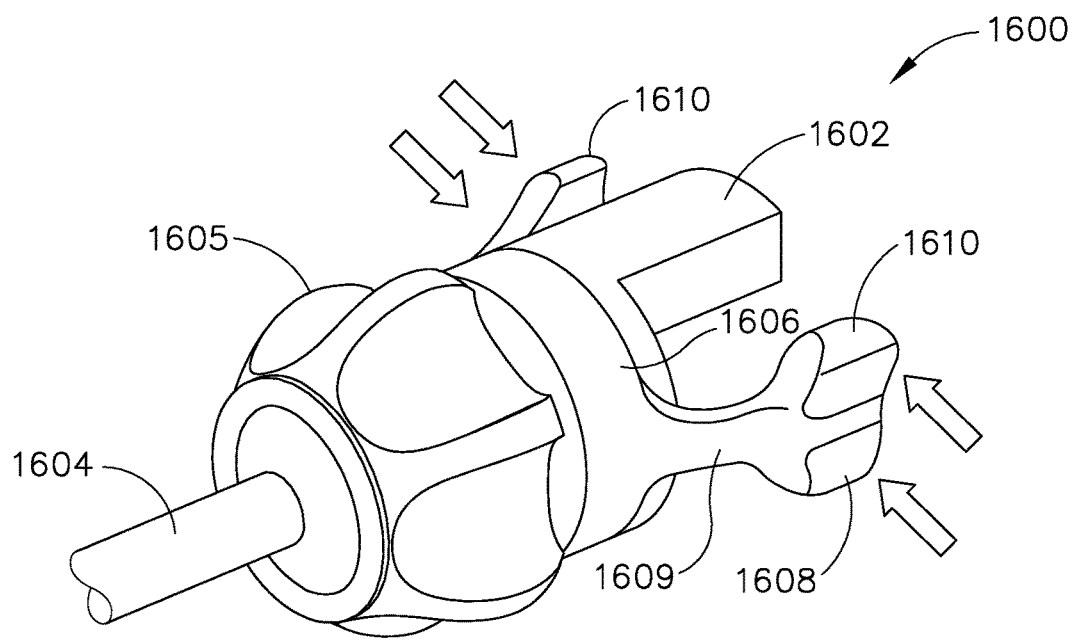
FIG. 20 depicts a perspective view of another exemplary shaft assembly configured to couple with the handpiece of FIG. 18.

FIG. 20 shows another merely exemplary shaft assembly (1600) that may be removably coupled with handpiece (1400). Shaft assembly (1600) comprises a control interface feature (1602) that is configured for receipt in socket (1406) of handpiece (1000). Shaft assembly (1600) also includes a distally extending shaft (1604) and an optional knob (1605) that is operable to rotate shaft (1604). An end effector (not shown) at the distal end of shaft (1604) may include numerous components, including but not limited to a stapling assembly, an ultrasonic blade, RF electrodes, etc. Components of the end effector may be driven by the drive features within handpiece (1400), with the electrical/acoustic/mechanical/etc. actuation being communicated through socket (1406), control interface feature (1602), and shaft (1604).

In the present example, shaft (1604) also includes an articulation section that is operable to selectively deflect the end effector laterally away from the longitudinal axis of shaft (1604). This articulation is controlled by buttons (1608, 1610) of shaft assembly (1610). Buttons (1608, 1610) are positioned at the free ends of opposing arms (1609), which are secured to a ring (1606). In the present example, ring (1606) is not rotatable, though it should be understood that ring (1606) may be rotatable in other versions to provide another form of user input to drive the end effector, etc. Buttons (1608, 1610) are configured to be pressed inwardly and are positioned at control zone (1420), such that the operator may press buttons (1608, 1610) using the same hand that grasps pistol grip (1404). When button (1608) is pressed, a drive feature in handpiece a drive feature in handpiece (1400) drives the end effector to deflect in a first lateral direction away from the longitudinal axis of shaft (1504)(e.g., to the left). When button (1610) is pressed, a drive feature in handpiece a drive feature in handpiece (1400) drives the end effector to deflect in a second lateral direction away from the longitudinal axis of shaft (1504) (e.g., to the right). In some other versions, both buttons (1608, 1610) at the end of one arm (1609) are operable to cause end effector articulation in the first lateral direction; while buttons (1608, 1610) at the end of the other arm (1609) are operable to cause end effector articulation in the second lateral direction. Other suitable responses that may be triggered by buttons (1608, 1610) will be apparent to those of ordinary skill in the art in view of the teachings herein.

Figure 21:
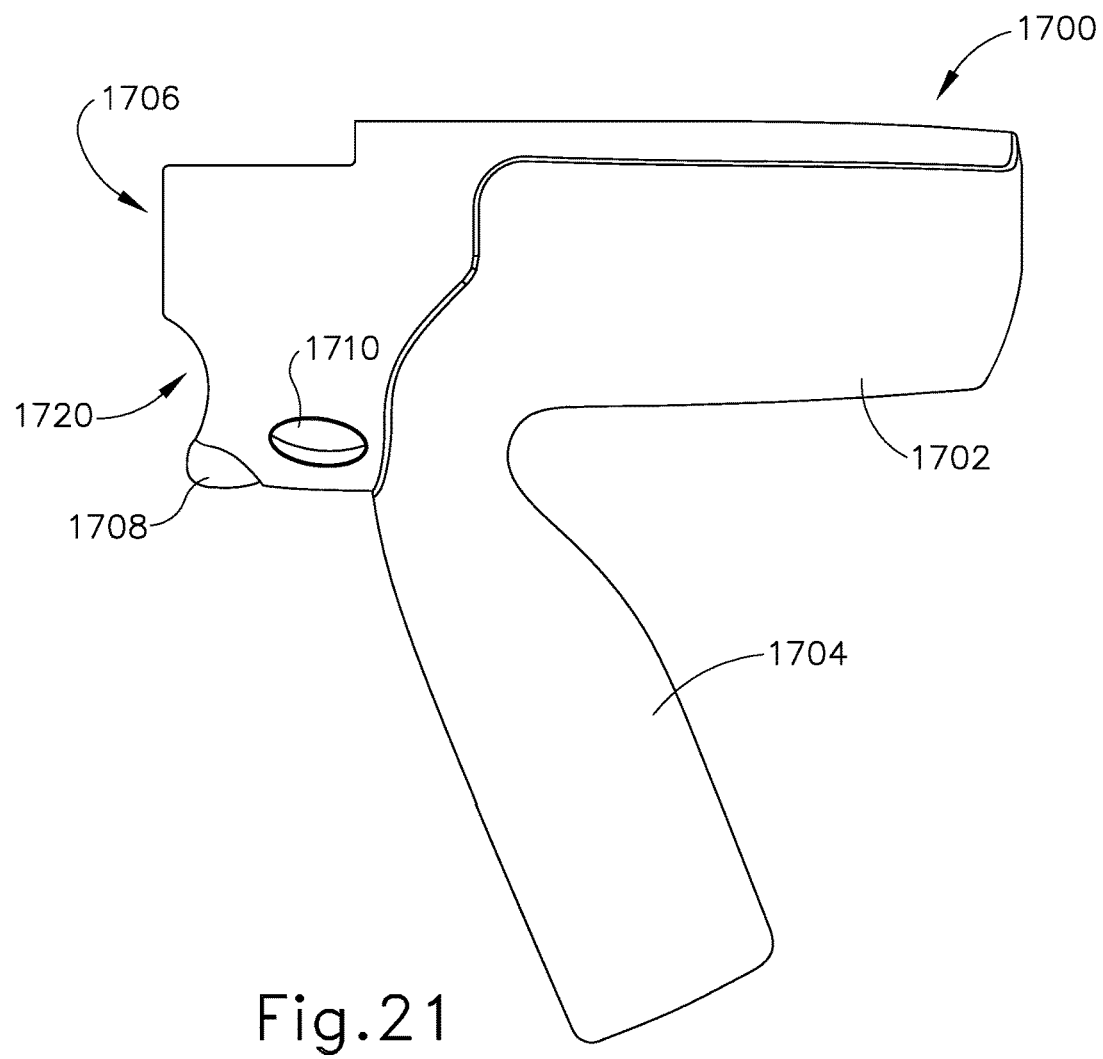
FIG. 21 depicts a side elevational view of another exemplary handpiece configured to receive a modular shaft assembly.

FIG. 21 shows yet another exemplary handpiece (1700) that is configured to couple with various exemplary shaft assemblies, including but not limited to shaft assemblies (1800, 1900, 2000) described below. Handpiece (1700) includes a housing (1702) that defines a pistol grip (1704) and a shaft socket (1706). While a pistol grip (1704) is provided by handpiece (1700) in this example, it should be understood that any other suitable kind of grip may be provided. Shaft socket (1706) is configured to receive a complementary control interface feature of a shaft assembly. Handpiece (1700) also includes various drive features that are operable to drive a shaft assembly via shaft socket (1706), such as electrical drive features (e.g., wires, battery, etc.), ultrasonic drive features (e.g., ultrasonic transducer, etc.), mechanical drive features (e.g., gears, motors, etc.), etc. In addition, handpiece (1700) includes a first activation button (1708) and a second activation button (1710), each of which are operable to selectively activate corresponding drive features in handpiece (1700). Handpiece (1400) of this example also includes a control zone (1720) associated with control inputs of attached shaft assemblies. Providing such a consistent location for control inputs of an attached shaft assembly may make operation of the instrument more intuitive and familiar for an operator. Of course, the designation of a control zone (1720) is merely optional.

Figure 22:
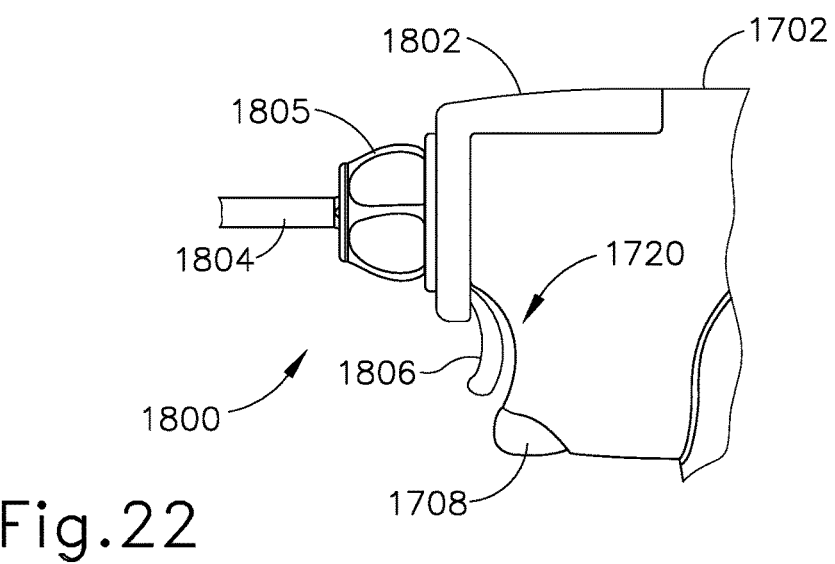
FIG. 22 depicts a side elevational view of an exemplary shaft assembly configured to couple with the handpiece of FIG. 21.

FIG. 22 shows one merely exemplary shaft assembly (1800) coupled with handpiece (1700). Shaft assembly (1800) comprises a control interface feature (not shown) that is disposed in socket (1706) of handpiece (1700). Shaft assembly (1800) also includes a distally extending shaft (1804) and an optional knob (1805) that is operable to rotate shaft (1804). An end effector (not shown) at the distal end of shaft (1804) may include numerous components, including but not limited to a stapling assembly, an ultrasonic blade, RF electrodes, etc. Components of the end effector may be driven by the drive features within handpiece (1700), with the electrical/acoustic/mechanical/etc. actuation being communicated through socket (1706), the control interface feature of shaft assembly (1800), and shaft (1804).

Shaft assembly (1800) of this example also includes a pivoting trigger (1806). Trigger (1806) is operable to selectively activate a drive feature in handpiece (1700). By way of example only, the end effector at the distal end of shaft (1804) may include clamping jaws and RF electrodes that are operable to apply bipolar RF energy to tissue clamped between the jaws. In some such versions, trigger (1806) may activate handpiece (1700) to drive the jaws to a closed position; while one or both of buttons (1708, 1710) may activate handpiece (1700) to provide RF energy to the electrodes of the jaws. Trigger (1806) is positioned at control zone (1720), such that the operator may pivot trigger (1806) using the same hand that grasps pistol grip (1704). Other suitable responses that may be triggered by trigger (1806) will be apparent to those of ordinary skill in the art in view of the teachings herein.

Figure 23:
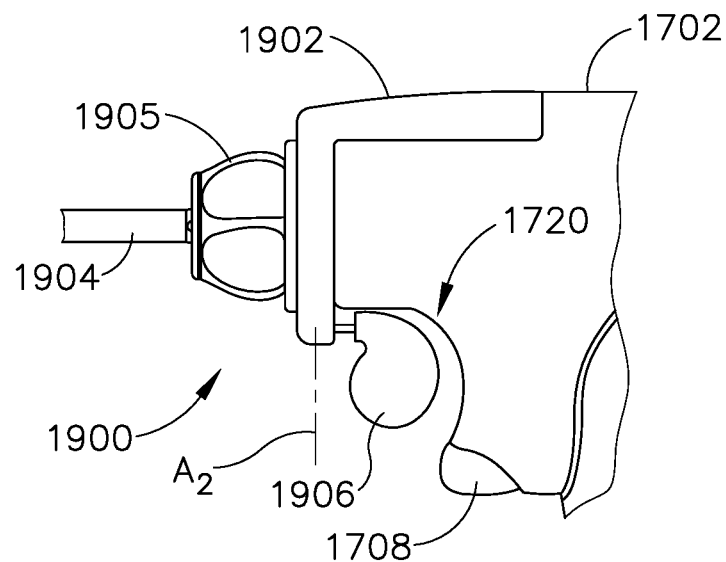
FIG. 23 depicts a side elevational view of another exemplary shaft assembly configured to couple with the handpiece of FIG. 21.

FIG. 23 shows another merely exemplary shaft assembly (1900) coupled with handpiece (1700). Shaft assembly (1900) comprises a control interface feature (not shown) that is disposed in socket (1706) of handpiece (1700). Shaft assembly (1900) also includes a distally extending shaft (1904) and an optional knob (1905) that is operable to rotate shaft (1904). An end effector (not shown) at the distal end of shaft (1904) may include numerous components, including but not limited to a stapling assembly, an ultrasonic blade, RF electrodes, etc. Components of the end effector may be driven by the drive features within handpiece (1700), with the electrical/acoustic/mechanical/etc. actuation being communicated through socket (1706), the control interface feature of shaft assembly (1900), and shaft (1904).

Shaft assembly (1900) of this example also includes a pivoting paddle (1906), which is pivotable about an axis ($A_2$). Paddle (1906) is operable to selectively activate drive features in handpiece (1700). By way of example only, shaft (1904) may include an articulation section that is operable to selectively deflect the end effector laterally away from the longitudinal axis of shaft (1904). Handpiece (1700) may include a drive feature that is operable to drive such articulation in response to pivoting of paddle (1906). Paddle (1906) is positioned at control zone (1720), such that the operator may pivot paddle (1906) using the same hand that grasps pistol grip (1704). Other suitable responses that may be triggered by paddle (1906) will be apparent to those of ordinary skill in the art in view of the teachings herein.

Figure 24:
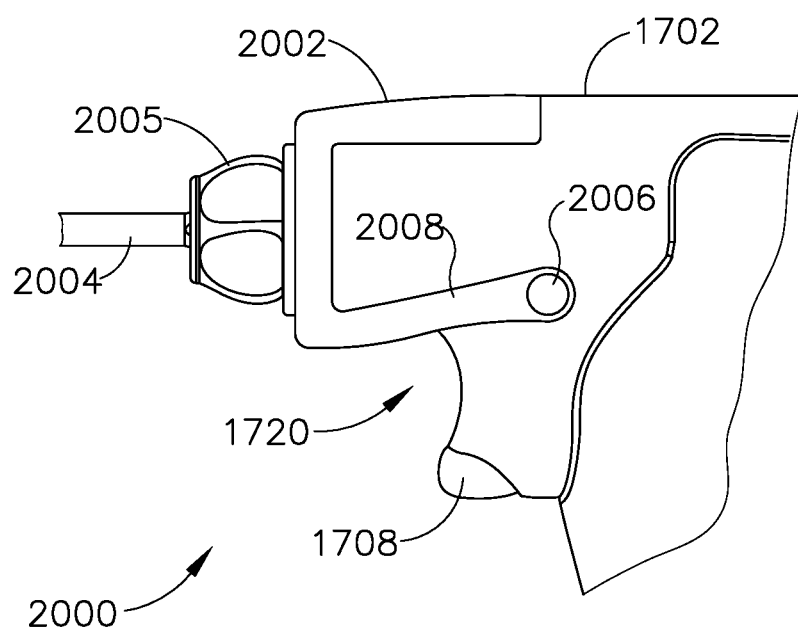
FIG. 24 depicts a side elevational view of another exemplary shaft assembly configured to couple with the handpiece of FIG. 21.

FIG. 24 shows another merely exemplary shaft assembly (2000) coupled with handpiece (1700). Shaft assembly (2000) comprises a control interface feature (not shown) that is disposed in socket (1706) of handpiece (1700). Shaft assembly (2000) also includes a distally extending shaft (2004) and an optional knob (2005) that is operable to rotate shaft (2004). An end effector (not shown) at the distal end of shaft (2004) may include numerous components, including but not limited to a stapling assembly, an ultrasonic blade, RF electrodes, etc. Components of the end effector may be driven by the drive features within handpiece (1700), with the electrical/acoustic/mechanical/etc. actuation being communicated through socket (1706), the control interface feature of shaft assembly (2000), and shaft (2004). Shaft assembly (2000) of this example also includes an activation button (2006) located at a proximal end of an arm (2008). Button (2006) is operable to activate a drive feature in handpiece to selectively drive an element in the end effector at the distal end of shaft (2004). Various suitable responses that may be triggered by button (2006) will be apparent to those of ordinary skill in the art in view of the teachings herein. It should also be understood that button (2006) is positioned just proximal to control zone (1720) in this example, such that the operator may press button (2006) using the same hand that grasps pistol grip (1704).

V. Miscellaneous

In any of the examples described herein, it should be understood that a footswitch may be used to selectively activate one or more features of the surgical instrument. By way of example only, such a footswitch may be directly coupled with generator (60). A footswitch may enable the operator to selectively activate one or more features of the surgical instrument simply by actuating the footswitch. In addition or in the alternative, the operator may need to actuate one or more user input features on the surgical instrument and actuate a footswitch simultaneously in order to selectively activate one or more features of the surgical instrument. Various other suitable ways in which a footswitch may be incorporated with the teachings herein will be apparent to those of ordinary skill in the art.

It should be understood that any of the versions of surgical instruments described herein may include various other features in addition to or in lieu of those described above. By way of example only, any of the devices herein may also include one or more of the various features disclosed in any of the various references that are incorporated by reference herein. It should also be understood that the teachings herein may be readily applied to any of the instruments described in any of the references cited herein, such that the teachings herein may be readily combined with the teachings of any of the references cited herein in numerous ways. Other types of instruments into which the teachings herein may be incorporated will be apparent to those of ordinary skill in the art.

Similarly, it should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should also be understood that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometric s, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical kit, comprising:
   a surgical instrument, wherein the surgical instrument comprises:
   a body having a first power socket and a body portion defining a first axis,
   a shaft extending distally from the body, wherein the shaft defines a longitudinal axis, wherein the longitudinal axis is offset from the first axis, and
   an end effector positioned at a distal end of the shaft and including an active feature configured to operate on tissue, wherein the active feature is selected from the group consisting of:
   an ultrasonic blade,
   at least one electrode operable to apply RF energy to the tissue, and
   a stapler;
   a battery selectively positioned within the first power socket along the longitudinal axis and transverse to the first axis of the body, wherein the active feature of the end effector is configured to operate based on electrical power from the battery when the battery is inserted in the first power socket; and
   a power cable having a first plug and a second plug, wherein the first plug is selectively positioned within the first power socket along the longitudinal axis and transverse to the first axis of body such that the first plug and the battery are removably interchangeable, wherein the second plug is configured to couple with an external power source, wherein the active feature of the end effector is configured to operate based on electrical power communicated through the power cable when the first plug is inserted in the power socket.

2. The kit of claim 1, further comprising a guide member configured to removably engage the body and thereby guide the battery or the first plug into the first power socket while maintaining sterility of the body.

3. The kit of claim 2, wherein the guide includes an outer wall and an inner wall, wherein the outer wall is configured to be grasped by a clinician, wherein the inner wall defines a passageway configured to pass the battery and the power cable through.

4. The kit of claim 3, wherein the inner wall is angled relative to the outer wall and thereby configured to guide the battery and the power cable into the passageway and toward the first power socket.

5. The kit of claim 1, wherein the first plug is sized and shaped identical to the battery to be received within the first power socket.

6. The kit of claim 1, wherein the surgical instrument further includes a latch configured to selectively secure the battery to the body, and wherein the latch is further configured to selectively secure the power cable to the body.

7. The kit of claim 1, wherein the battery is configured to cover the first power socket when the battery is positioned within the first power socket, and wherein the power cable is configured to cover the first power socket when the first plug is positioned within the first power socket.

8. The kit of claim 1, wherein the surgical instrument further includes a door connected to the body adjacent to the power socket, wherein the door is configured to move from a closed position to an opened position, wherein the door in the closed position is configured to cover the first power socket for containing the battery within the first power socket, and wherein the door in the opened position is configured to uncover the first power socket for receiving the battery with the first power socket.

9. A kit for a surgical instrument, comprising:
an end effector including an active feature configured to operate on tissue, wherein the active feature is selected from the group consisting of:
an ultrasonic blade,
at least one electrode operable to apply RF energy to the tissue, and
a stapler;
a shaft having a proximal end and a distal end, wherein the end effector is configured to be disposed at the distal end of the shaft, wherein the shaft defines a longitudinal axis;
a body configured to extend proximally from the shaft, wherein the body comprises:
a distal portion of the body, including:
a power interface feature configured to receive power interchangeably from at least two different kinds of electrical power sources, wherein the at least two different kinds of electrical power sources comprise a cordless battery and a corded electrical power source, wherein the cordless battery is interchangeable with the corded electrical power source for power delivery to the power interface, and wherein the corded electrical power source is interchangeable with the cordless battery for power delivery to the power interface, and
a drive feature responsive to electrical power and configured to drive the active feature of the end effector, wherein the drive feature is configured to receive electrical power from the power interface feature, wherein the drive feature is operable to drive the active feature of the end effector based on electrical power from one of the at least two different kinds of electrical power sources coupled with the power interface feature,
a first proximal portion of the body configured to removably connect to the distal portion of the body, wherein the first proximal portion of the body includes the cordless battery, wherein an exterior surface of the cordless battery defines a full pistol grip for grasping during operation of the end effector,
a second proximal portion of the body configured to removably connect to the distal portion of the body, wherein the second proximal portion of the body includes the corded electrical power source, wherein an exterior surface of the corded electrical power source defines a full pistol grip for grasping during operation of the end effector,
wherein the first and second proximal portion of the body are selectively interchangeable whereby the first proximal portion and the distal portion are configured to define the body when the first proximal portion is coupled with the distal portion such that at least a portion of the cordless battery is positioned along a transverse axis that is transverse to the longitudinal axis, and whereby the second proximal portion and the distal portion are configured to define the body when the second proximal portion is coupled with the distal portion such that at least a portion of the corded electrical power source is positioned along the transverse axis that is transverse to the longitudinal axis.

10. The kit of claim 9, wherein the power interface feature includes a socket configured to respectively receive each of the cordless battery and the corded electrical power source to respectively electrically connect the power interface to the cordless battery or the corded electrical power.

11. The kit of claim 9, wherein the power interface is configured to transmit data respectively between the distal portion of the body and each of the first proximal portion of the body and the second proximal portion of the body.

12. The kit of claim 11, wherein the distal portion of the body further includes a control module, wherein the control module is configured to respectively receive data from the first and second proximal portions of the body via the power interface feature, and wherein the control module is configured to respectively communicate data to the first and second proximal portions of the body via the power interface feature.

13. The kit of claim 9, wherein the shaft is configured to extend longitudinally from the body, wherein each of the first proximal portion and the second proximal portion include a longitudinal portion extending along the longitudinal axis.

14. The kit of claim 13, wherein each of the first proximal portion and the second proximal portion further include a transverse portion extending along the transverse axis, wherein the transverse axis intersects the longitudinal axis.

15. The kit of claim 9, wherein the shaft is configured to extend longitudinally from the body, wherein the remainder of the pistol grip of each of the first and second proximal portions of the body includes a transverse portion extending along the transverse axis.

16. The kit of claim 15, wherein the remainder of the pistol grip of each of the first and second proximal portions of the body includes a longitudinal portion extending along the longitudinal axis, wherein the transverse axis intersects the longitudinal axis.

17. A kit for a surgical instrument, comprising:
an end effector including an active feature configured to operate on tissue, wherein the active feature is selected from the group consisting of:
an ultrasonic blade,
at least one electrode operable to apply RF energy to the tissue, and
a stapler;
a shaft having a proximal end and a distal end, wherein the end effector is configured to be disposed at the distal end of the shaft, wherein the shaft defines a longitudinal axis;
a body configured to extend proximally from the shaft, wherein the body comprises:
a distal portion of the body defining a first partial portion of a pistol grip, wherein the distal portion includes:
a power interface feature configured to receive power interchangeably from at least two different kinds of electrical power sources, wherein the at least two different kinds of electrical power sources comprise a cordless battery and a corded electrical power source, wherein the cordless battery is interchangeable with the corded electrical power source for power delivery to the power interface, wherein the corded electrical power source is interchangeable with the cordless battery for power delivery to the power interface, and a drive feature responsive to electrical power and configured to drive the active feature of the end effector, wherein the drive feature is configured to receive electrical power from the power interface feature, wherein the drive feature is operable to drive the active feature of the end effector based on electrical power from one of the at least two different kinds of electrical power sources coupled with the power interface feature, a first proximal portion of the body configured to removably connect to the distal portion of the body, wherein the first proximal portion of the body includes the cordless battery, wherein an exterior surface of the cordless battery defines a first remainder of the pistol grip, a second proximal portion of the body configured to removably connect to the distal portion of the body, wherein the second proximal portion of the body includes the corded electrical power source, wherein an exterior surface of the corded electrical power source defines a second remainder of the pistol grip, wherein the first and second proximal portion of the body are selectively interchangeable whereby the first proximal portion and the distal portion are configured to define the body as a first entirety of the pistol grip when the first remainder of the pistol grip of the first proximal portion is coupled with the first partial portion of the pistol grip of the distal portion such that the cordless battery is positioned along a transverse axis that is transverse to the longitudinal axis, and whereby the second proximal portion and the distal portion are configured to define the body as a second entirety of the pistol grip when the second remainder of the pistol grip of the second proximal portion is coupled with the first partial portion of the pistol grip of the distal portion such that the corded electrical power source is positioned along the transverse axis that is transverse to the longitudinal axis.

18. The kit of claim 17, wherein the distal portion includes a longitudinal portion extending along the longitudinal axis.

19. The kit of claim 18, wherein the first partial portion of the pistol grip of the distal portion includes a transverse portion extending along the transverse axis that is transverse to the longitudinal axis.

20. The kit of claim 19, wherein the remainder of the pistol grip of each of the first and second proximal portions of the body includes a transverse portion extending along the transverse axis downward of the first partial portion of the pistol grip.

* * * * *